(12) United States Patent
Jarjour et al.

(10) Patent No.: US 12,016,314 B2
(45) Date of Patent: Jun. 25, 2024

(54) MICRORNA INHIBITOR THERAPY IN SYSTEMIC LUPUS ERYTHEMATOSUS

(71) Applicant: Ohio State Innovation Foundation, Columbus, OH (US)

(72) Inventors: Wael N. Jarjour, Columbus, OH (US); Giancarlo Valiente, Columbus, OH (US); Nicholas Young, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 660 days.

(21) Appl. No.: 16/645,656

(22) PCT Filed: Sep. 10, 2018

(86) PCT No.: PCT/US2018/050172
§ 371 (c)(1),
(2) Date: Mar. 9, 2020

(87) PCT Pub. No.: WO2019/051355
PCT Pub. Date: Mar. 14, 2019

(65) Prior Publication Data
US 2020/0281174 A1      Sep. 10, 2020

Related U.S. Application Data

(60) Provisional application No. 62/556,187, filed on Sep. 8, 2017.

(51) Int. Cl.
*A01K 67/027* (2024.01)
*A01K 67/0278* (2024.01)
(Continued)

(52) U.S. Cl.
CPC ...... *A01K 67/0278* (2013.01); *A61K 31/7105* (2013.01); *C12N 15/113* (2013.01);
(Continued)

(58) Field of Classification Search
CPC .............. A61K 31/7105; C12N 15/113; C12N 2310/3231
See application file for complete search history.

(56) References Cited

U.S. PATENT DOCUMENTS 4,452,901 A   6/1984 Gordon et al.
4,897,355 A   1/1990 Eppstein et al.
(Continued)

FOREIGN PATENT DOCUMENTS

WO   92/03566   3/1992
WO   93/22434   11/1993
(Continued)

OTHER PUBLICATIONS

Ugalde et al. (The EMBO Journal, 2011 vol. 30:2219-2232).*
(Continued)

*Primary Examiner* — Terra C Gibbs
(74) *Attorney, Agent, or Firm* — Meunier Carlin & Curfman LLC

(57) ABSTRACT

Disclosed are novel compositions and methods for treating systemic lupus erythematosus (SLE) as well as a model for measuring the efficacy of said treatments. Specifically, the disclosure provides a non-human animal model for SLE comprising a severe combined immunodeficient non-human animal comprising exogenous cells from a human subject with SLE, wherein the cells from the human subject are peripheral blood mononuclear cells. Further disclosed is a method of screening for a drug candidate that inhibits or reduces SLE using a severe combined immunodeficient non-human animal.

3 Claims, 21 Drawing Sheets
Specification includes a Sequence Listing.

(51) Int. Cl.
*A61K 31/7105* (2006.01)
*C12N 15/113* (2010.01)

(52) U.S. Cl.
CPC .... *A01K 2207/12* (2013.01); *A01K 2217/075* (2013.01); *A01K 2227/105* (2013.01); *A01K 2267/0325* (2013.01); *C12N 2310/113* (2013.01); *C12N 2310/3231* (2013.01)

(56) References Cited

U.S. PATENT DOCUMENTS

| | | |
|---|---|---|
| 5,135,917 A | 8/1992 | Burch |
| 5,168,053 A | 12/1992 | Altman |
| 5,176,996 A | 1/1993 | Hogan |
| 5,294,533 A | 3/1994 | Lupski et al. |
| 5,334,711 A | 8/1994 | Sproat et al. |
| 5,424,000 A | 6/1995 | Winicov et al. |
| 5,436,330 A | 7/1995 | Taira et al. |
| 5,476,766 A | 12/1995 | Gold et al. |
| 5,503,978 A | 4/1996 | Schneider |
| 5,543,293 A | 8/1996 | Gold et al. |
| 5,580,737 A | 12/1996 | Polisky et al. |
| 5,580,967 A | 12/1996 | Joyce |
| 5,595,873 A | 1/1997 | Joyce |
| 5,616,466 A | 4/1997 | Cantor et al. |
| 5,624,824 A | 4/1997 | Yuan et al. |
| 5,627,158 A | 5/1997 | Cho-Chung |
| 5,631,115 A | 5/1997 | Ohtsuka et al. |
| 5,631,146 A | 5/1997 | Szostak et al. |
| 5,633,133 A | 5/1997 | Long et al. |
| 5,641,754 A | 6/1997 | Iversen |
| 5,645,985 A | 7/1997 | Froehler et al. |
| 5,646,020 A | 7/1997 | Swiggen et al. |
| 5,646,031 A | 7/1997 | Deyoung et al. |
| 5,646,042 A | 7/1997 | Stinchcomb et al. |
| 5,650,316 A | 7/1997 | Aggarwal et al. |
| 5,652,094 A | 7/1997 | Usman et al. |
| 5,652,107 A | 7/1997 | Lizardi et al. |
| 5,683,873 A | 11/1997 | George et al. |
| 5,683,874 A | 11/1997 | Kool et al. |
| 5,683,902 A | 11/1997 | Hampel et al. |
| 5,688,670 A | 11/1997 | Szostak et al. |
| 5,691,317 A | 11/1997 | Cho-Chung |
| 5,693,535 A | 12/1997 | Draper et al. |
| 5,693,773 A | 12/1997 | Kandimalla et al. |
| 5,712,384 A | 1/1998 | Symonds et al. |
| 5,728,521 A | 3/1998 | Yuan et al. |
| 5,731,295 A | 3/1998 | Draper et al. |
| 5,731,424 A | 3/1998 | Toothman et al. |
| 5,770,715 A | 6/1998 | Sugiyama et al. |
| 5,780,228 A | 7/1998 | Parma et al. |
| 5,780,607 A | 7/1998 | Goodnow, Jr. et al. |
| 5,786,138 A | 7/1998 | Swenson et al. |
| 5,786,462 A | 7/1998 | Schneider et al. |
| 5,792,613 A | 8/1998 | Schmidt et al. |
| 5,795,721 A | 8/1998 | Rabin et al. |
| 5,807,718 A | 9/1998 | Joyce et al. |
| 5,811,300 A | 9/1998 | Sullivan et al. |
| 5,834,185 A | 11/1998 | Ts'o et al. |
| 5,837,855 A | 11/1998 | Chowrira et al. |
| 5,846,713 A | 12/1998 | Pagratis et al. |
| 5,849,903 A | 12/1998 | Pietrzkowski et al. |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schneider et al. |
| 5,861,288 A | 1/1999 | Usman et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,162 A | 3/1999 | Werner et al. |
| 5,891,683 A | 4/1999 | Usman et al. |
| 5,891,684 A | 4/1999 | Usman et al. |
| 5,910,408 A | 6/1999 | Szostak et al. |
| 5,919,772 A | 7/1999 | Szyf et al. |
| 5,955,590 A | 9/1999 | Levina et al. |
| 5,958,691 A | 9/1999 | Pieken et al. |
| 5,962,426 A | 10/1999 | Glazer |
| 5,972,699 A | 10/1999 | Draper |
| 5,972,704 A | 10/1999 | Draper et al. |
| 5,985,621 A | 11/1999 | Usman et al. |
| 5,989,906 A | 11/1999 | Thompson |
| 5,989,908 A | 11/1999 | Scanlon |
| 5,990,088 A | 11/1999 | Ensoli et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence et al. |
| 6,001,988 A | 12/1999 | Parma et al. |
| 6,005,095 A | 12/1999 | Capaccioli et al. |
| 6,007,995 A | 12/1999 | Baker et al. |
| 6,011,020 A | 1/2000 | Gold et al. |
| 6,013,443 A | 1/2000 | Heilig et al. |
| 6,013,522 A | 1/2000 | Monia et al. |
| 6,017,756 A | 1/2000 | Draper |
| 6,017,898 A | 1/2000 | Pietrzkowski et al. |
| 6,020,130 A | 2/2000 | Gold et al. |
| 6,022,962 A | 2/2000 | Chowrira et al. |
| 6,025,198 A | 2/2000 | Bennett et al. |
| 6,028,186 A | 2/2000 | Tasset et al. |
| 6,030,776 A | 2/2000 | Eaton et al. |
| 6,033,910 A | 3/2000 | Monia et al. |
| 6,040,296 A | 3/2000 | Nyce |
| 6,046,004 A | 4/2000 | Wu et al. |
| 6,046,319 A | 4/2000 | Power et al. |
| 6,051,698 A | 4/2000 | Janjic et al. |
| 6,057,437 A | 5/2000 | Kamiya et al. |
| 6,261,834 B1 | 7/2001 | Srivastava |
| 7,176,303 B2 * | 2/2007 | Freier ............... A61P 35/00 435/6.12 |
| 8,501,703 B2 * | 8/2013 | Bennett ............ C12N 15/1135 536/24.31 |
| 9,157,081 B2 * | 10/2015 | Bennett ............... C12N 15/111 |
| 2004/0109876 A1 | 6/2004 | Yamamoto et al. |
| 2014/0101786 A1 | 4/2014 | Sykes et al. |

FOREIGN PATENT DOCUMENTS

| | | | |
|---|---|---|---|
| WO | 95/24489 | 9/1995 | |
| WO | 97/18312 | 5/1997 | |
| WO | 98/58057 | 12/1998 | |
| WO | 98/58058 | 12/1998 | |
| WO | WO-2005013901 A2 * | 2/2005 | ............... A61P 3/00 |
| WO | WO-2008116267 A1 * | 10/2008 | .......... C12N 15/113 |
| WO | 2013013165 | 1/2013 | |

OTHER PUBLICATIONS

Li et al. (Molecular Pharmacology, 2011 vol. 80:191-2000).*
Maegdefessel et al. (The Journal of Clinical Investigations, 2012 vol. 122:497-506).*
Fabbri et al. (PNAS, 2012 vol. 109:e2110-e2116, plus Supplementary Information).*
Green et al. (PLOS ONE, 2015 vol. 10:1-20).*
Li et al. (Molecular Pharmacology, 2011 vol. 80:191-200, plus Supplemental Data).*
Zhi Abstract (Acta Pharmaceutica Sinica, May 1, 2009, 44(5): Abstract Only).*
Rothschild et al. (Oncogene (2012) vol. 31: 4221-4232).*
Anderson, Leigh, and Norman G. Anderson. "High resolution two-dimensional electrophoresis of human plasma proteins." Proceedings of the National Academy of sciences 74.12 (1977): 5421-5425.

(56) References Cited

OTHER PUBLICATIONS

Bagshawe, K. D. "Towards generating cytotoxic agents at cancer sites. The First Bagshawe Lecture." Br. J. Cancer 60 (1989): 275-281.
Bagshawe, K. D., et al. "A cytotoxic agent can be generated selectively at cancer sites." British journal of cancer 58.6 (1988): 700-703.
Banerji, Julian, Laura Olson, and Walter Schaffner. "A lymphocyte-specific cellular enhancer is located downstream of the joining region in immunoglobulin heavy chain genes." Cell 33.3 (1983): 729-740.
Battelli, M. G., et al. "T lymphocyte killing by a xanthine-oxidase-containing immunotoxin." Cancer Immunology, Immunotherapy 35.6 (1992): 421-425.
Berkner, Kathleen L., et al. "Abundant expression of polyomavirus middle T antigen and dihydrofolate reductase in an adenovirus recombinant." Journal of virology 61.4 (1987): 1213-1220.
Bout, Abraham, et al. "Lung gene therapy: in vivo adenovirus-mediated gene transfer to rhesus monkey airway epithelium." Human gene therapy 5.1 (1994): 3-10.
Brigham, Kenneth L., et al. "Expression of a prokaryotic gene in cultured lung endothelial cells after lipofection with a plasmid vector." Am J Respir Cell Mol Biol 1.2 (1989): 95-100.
Brown, Dennis T., and Byron T. Burlingham. "Penetration of host cell membranes by adenovirus 2." Journal of virology 12.2 (1973): 386-396.
Brown, Valerie I., and Mark I. Greene. "Molecular and cellular mechanisms of receptor-mediated endocytosis." DNA and cell biology 10.6 (1991): 399-409.
Caillaud, Catherine, et al. "Adenoviral vector as a gene delivery system into cultured rat neuronal and glial cells." European Journal of Neuroscience 5.10 (1993): 1287-1291.
Carrara, Gioia, et al. "Two helices plus a linker: a small model substrate for eukaryotic RNase P." Proceedings of the National Academy of Sciences 92.7 (1995): 2627-2631.
Chardonnet, Yvette, and Samuel Dales. "Early events in the interaction of adenoviruses with Hela cells: I. Penetration of type 5 and intracellular release of the DNA genome." Virology 40.3 (1970): 462-477.
Cotter, Murray A., and E. S. Robertson. "Molecular genetic analysis of herpesviruses and their potential use as vectors for gene therapy applications." Current opinion in molecular therapeutics 1.5 (1999): 633.
Davidson, Dominique, and John A. Hassell. "Overproduction of polyomavirus middle T antigen in mammalian cells through the use of an adenovirus vector." Journal of virology 61.4 (1987): 1226-1239.
Fabbri M, Paone A, Calore F, Galli R, Gaudio E, Santhanam R et al. MicroRNAs bind to Tolllike receptors to induce prometastatic inflammatory response. Proceedings of the National Academy of Sciences of the United States of America, 2012;109:E21106.
Felgner, Philip L., et al. "Lipofection: a highly efficient, lipid-mediated DNA-transfection procedure." Proceedings of the National Academy of Sciences 84.21 (1987): 7413-7417.
Fiers, Walter, et al. "Complete nucleotide sequence of SV40 DNA." Nature 273.5658 (1978): 113-120.
Forster and Altman, "External Guide Sequences for an RNA Enzyme", Science 238:407-409 (1990).
Gomez-Foix, Anna M., et al. "Adenovirus-mediated transfer of the muscle glycogen phosphorylase gene into hepatocytes confers altered regulation of glycogen metabolism." Journal of Biological Chemistry 267.35 (1992): 25129-25134.
Greenaway, P. J., et al. "Human cytomegalovirus DNA: BamHI, EcoRI and PstI restriction endonuclease cleavage maps." Gene 18.3 (1982): 355-360.
Guzman, et al., "Efficient Gene Transfer Into Myocardium by Direct Injection of Adenovirus Vectors" Circulation Research 73:1202-1207 (1993).
Haj-Ahmad, Yousef, and Frank L. Graham. "Development of a helper-independent human adenovirus vector and its use in the transfer of the herpes simplex virus thymidine kinase gene." Journal of virology 57.1 (1986): 267-274.
Handbook of Monoclonal Antibodies, Ferrone et al., eds., Noges Publications, Park Ridge, N.J., (1985) ch. 22 and pp. 303-357.
Hughes, Brenda J., et al. "Monoclonal antibody targeting of liposomes to mouse lung in vivo." Cancer research 49.22 (1989): 6214-6220.
Ikuta et al., "Synthesis and Use of Synthetic Oligonucleotides "Ann. Rev. Biochem. 53:323-356 (1984).
Kirshenbaum, Lorrie A., et al. "Highly efficient gene transfer into adult ventricular myocytes by recombinant adenovirus." The Journal of clinical investigation 92.1 (1993): 381-387.
La Salle, G. Le Gal, et al. "An adenovirus vector for gene transfer into neurons and glia in the brain." Science 259.5097 (1993): 988-990.
Laemmli, U.K., Cleavage of structural proteins during the assembly of the head of bacteriophage T4, Nature 227:680 (1970).
Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.
Litzinger and Huang, Biochimica et Biophysica Acta, 1104:179-187, (1992).
Lusky, M. O. N. I. K. A., et al. "Bovine papilloma virus contains an activator of gene expression at the distal end of the early transcription unit." Molecular and Cellular Biology 3.6 (1983): 1108-1122.
Massie, Bernard, Y. Gluzman, and J. A. Hassell. "Construction of a helper-free recombinant adenovirus that expresses polyomavirus large T antigen." Molecular and cellular biology 6.8 (1986): 2872-2883.
Matsudaira, P. T., and D. R. Burgess. "SDS microslab linear gradient polyacrylamide gel electrophoresis." Analytical biochemistry 87.2 (1978): 386-396.
Morsy, Manal A., et al. "Efficient adenoviral-mediated ornithine transcarbamylase expression in deficient mouse and human hepatocytes." The Journal of clinical investigation 92.3 (1993): 1580-1586.
Moullier, Philippe, et al. "Correction of lysosomal storage in the liver and spleen of MPS VII mice by implantation of genetically modified skin fibroblasts." Nature genetics 4.2 (1993): 154-159.
Mulligan, R.C. and Berg, P. Science 209: 1422 (1980).
Narang, S. A_, et al. "[61] Chemical synthesis of deoxyoligonucleotides by the modified triester method." Methods in Enzymology. vol. 65. Academic Press, 1980. 610-620.
Needleman, Saul B., and Christian D. Wunsch. "A general method applicable to the search for similarities in the amino acid sequence of two proteins." Journal of molecular biology 48.3 (1970): 443-453.
Neuhoff et al., Electrophoresis 6:427-448 (1985).
Neuhoff et al., Electrophoresis 9:255-262 (1988).
Nielsen, Peter E., Michael Egholm, and Ole Buchardt. "Peptide nucleic acid (PNA). A DNA mimic with a peptide backbone." Bioconjugate chemistry 5.1 (1994): 3-7.
O'Farrell, P.H., High Resolution Two-dimensional Electrophoresis of Proteins, J. Biol. Chem. 250:4007-4021 (1975).
Ornstein, L., Disc electrophoresis, L. Ann. N.Y. Acad. Sci. 121:321-349 (1964).
Osborne, T.F., et al., Mol. Cell Bio. 4: 1293 (1984).
Pearson, William R., and David J. Lipman. "Improved tools for biological sequence comparison." Proceedings of the National Academy of Sciences 85.8 (1988): 2444-2448.
Pietersz, Geoffrey A., and Ian FC Mckenzie. "Antibody conjugates for the treatment of cancer." Immunological reviews 129.1 (1992): 57-80.
Ragot, T., et al. "Replication-defective recombinant adenovirus expressing the Epstein-Barr virus (EBV) envelope glycoprotein gp340/220 induces protective immunity against EBV-induced lymphomas in the cottontop tamarin." Journal of General Virology 74.3 (1993): 501-507.
Ram, Zvi, et al. "In situ retroviral-mediated gene transfer for the treatment of brain tumors in rats." Cancer Research 53.1 (1993): 83-88.
Rich, Devra P., et al. "Development and analysis of recombinant adenoviruses for gene therapy of cystic fibrosis." Human gene therapy 4.4 (1993): 461-476.

(56) References Cited

OTHER PUBLICATIONS

Roessler, J. Clin. Invest. 92:1085-1092 (1993).
Roffler, et al., Biochem. Pharmacol, 42:2062-2065, (1991).
Salama A, Fichou N, Allard M, Dubreil L, De Beaurepaire L, Viel A et al. MicroRNA29b Modulates innate and antigen specific immune responses in mouse models of autoimmunity. PloS one, 2014;9:e106153.
Senter, et al., Bioconjugate Chem., 2:447-451, (1991).
Senter, et al., Bioconjugate Chem., 4:3-9, (1993).
Seth, et al., J. Virol. 51:650-655 (1984).
Seth, et al., Mol. Cell. Biol. 4:1528-1533 (1984).
Smith, Temple F., and Michael S. Waterman. "Comparison of biosequences." Advances in applied mathematics 2.4 (1981): 482-489.
Smith et al., Antibodies in Human Diagnosis and Therapy, Haber et al., eds., Raven Press, New York (1977) pp. 365-389.
Southern P. and Berg, P., J. Molec. Appl. Genet. 1: 327 (1982).
Sugden, B et al., Mol. Cell. Biol. 5: 410-413 (1985).
Sun, Tian-Qiang, David A. Fenstermacher, and Jean-Michel H. Vos. "Human artificial episomal chromosomes for cloning large DNA fragments in human cells." Nature genetics 8.1 (1994): 33-41.
Svensson and Persson, J. Virology 55:442-449 (1985).
Varga et al., J. Virology 65:6061-6070 (1991).
Wickham, Thomas J., et al. "Integrins $\alpha v\beta 3$ and $\alpha v\beta 5$ promote adenovirus internalization but not virus attachment." Cell 73.2 (1993): 309-319.
Acsadi, Gyula, et al. "Human dystrophin expression in mdx mice after intramuscular injection of DNA constructs." Nature 352.6338 (1991): 815-818.
Wolff, Jon A., et al. "Direct gene transfer into mouse muscle in vivo." Science 247.4949 (1990): 1465-1468.
Young NA, Wu LC, Burd CJ, Friedman AK, Kaffenberger BH, Rajaram MV et al. Estrogen modulation of endosome-associated toll-like receptor 8: An IFNalpha-independent mechanism of sex-bias in systemic lupus erythematosus. Clinical immunology, 2014; 151:66-77.
Young, et al., A chimeric human-mouse model of Sjögren's syndrome. Clinical Immunology (2015) 156, 1-8.
Yuan, Yan, and Sidney Altman. "Substrate recognition by human RNase P: identification of small, model substrates for the enzyme." The EMBO journal 14.1 (1995): 159-168.
Yuan, Yan, Eun-Seong Hwang, and Sidney Altman. "Targeted cleavage of mRNA by human RNase P." Proceedings of the National Academy of Sciences 89.17 (1992): 8006-8010.
Zabner, Cell 75:207-216 (1993).
Zabner, Nature Genetics 6:75-83 (1994).
Zhang, W. W., et al. "Generation and identification of recombinant adenovirus by liposome-mediated transfection and PCR analysis." Biotechniques 15.5 (1993): 868. Abstract.
International Preliminary Report on Patentability issued PCT/US2018/050172, dated Mar. 19, 2020.
International Search Report and Written Opinion issued by the International Searching Authority (ISA/US) in PCT Application No. PCT/US2018/050172 on Jan. 15, 2019. 15 pages.
Andrade, Danieli, et al. "Engraftment of PBMC from SLE and APS donors into BALB-Rag2-/- IL2Rgc-/- mice: A promising model for studying human disease." Arthritis and rheumatism 63.9 (2011): 2764.
Samata, Bumpei, et al. "X-linked severe combined immunodeficiency (X-SCID) rats for xeno-transplantation and behavioral evaluation." Journal of neuroscience methods 243 (2015): 68-77.
Kerekov, Nikola S., et al. "Elimination of autoreactive B cells in humanized SCID mouse model of SLE." European Journal of immunology 41.11 (2011): 3301-3311.
Celhar, Teja, and Anna-Marie Fairhurst. "Modelling clinical systemic lupus erythematosus: similarities, differences and success stories." Rheumatology 56.suppl_1 (2017): i88-i99.
Weidenbusch, Marc, Onkar P. Kulkarni, and Hans-Joachim Anders. "The innate immune system in human systemic lupus erythematosus." Clinical Science 131.8 (2017): 625-634.

\* cited by examiner

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: synthetic construct

<400> SEQUENCE: 1
caacatcagt ctgataagct                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic construct
```

```
<400> SEQUENCE: 2
aaccgatttc agatggtgct                                               20

<210> SEQ ID NO 3
<211> LENGTH: 19
<212> TYPE: DNA
<213> ORGANISM: Artificial Sequence
<220> FEATURE:
<223> OTHER INFORMATION: synthetic construct

<400> SEQUENCE: 3
actgatttca aatggtgct                                                19

<210> SEQ ID NO 4
<211> LENGTH: 25
<212> TYPE: DNA
<213> ORGANISM: Artificial Sequence
<220> FEATURE:
<223> OTHER INFORMATION: synthetic construct

<400> SEQUENCE: 4
gggagaatct aggtcaaggt ccttc                                         25

<210> SEQ ID NO 5
<211> LENGTH: 22
<212> TYPE: DNA
<213> ORGANISM: Artificial Sequence
<220> FEATURE:
<223> OTHER INFORMATION: synthetic construct

<400> SEQUENCE: 5
gaaggacctt gacctagatt ct                                            22

<210> SEQ ID NO 6
<211> LENGTH: 26
<212> TYPE: DNA
<213> ORGANISM: Artificial Sequence
<220> FEATURE:
<223> OTHER INFORMATION: synthetic construct

<400> SEQUENCE: 6
gggctttatt ctctgaaaca cccact                                        26

<210> SEQ ID NO 7
<211> LENGTH: 23
<212> TYPE: DNA
<213> ORGANISM: Artificial Sequence
<220> FEATURE:
<223> OTHER INFORMATION: synthetic construct

<400> SEQUENCE: 7
agtgggtgtt tcagagaata aag                                           23

<210> SEQ ID NO 8
<211> LENGTH: 22
<212> TYPE: RNA
<213> ORGANISM: Artificial Sequence
<220> FEATURE:
<223> OTHER INFORMATION: synthetic construct

<400> SEQUENCE: 8
uagcuuauca gacugauguu ga                                            22

<210> SEQ ID NO 9
```

```
<211> LENGTH: 19
<212> TYPE: RNA
<213> ORGANISM: Artificial Sequence
<220> FEATURE:
<223> OTHER INFORMATION: synthetic construct

<400> SEQUENCE: 9
uaaggcuaug aagagauac                                                    19
```

MICRORNA INHIBITOR THERAPY IN SYSTEMIC LUPUS ERYTHEMATOSUS

CROSS-REFERENCE TO RELATED APPLICATIONS

This application is a national stage application filed under 35 U.S.C. § 371 of PCT/US2018/050172 filed Sep. 10, 2018, which claims the benefit of U.S. Provisional Application No. 62/556,187, filed on Sep. 8, 2017 applications which are incorporated herein by reference in their entireties.

I. BACKGROUND

Systemic Lupus Erythematosus (SLE) is a prototypic chronic autoimmune disease affecting multiple organs with an unknown cause. Despite significant research into SLE, effective targeted therapies in SLE are lacking. Present treatments such as corticosteroids, methotrexate, hydroxycholorquine and immunosuppressants, and non-steroidal antiinflammatory drugs non-specifically inhibit symptoms rather than precisely attacking the disorder. Moreover, current non-human animal models do not translate efficaciously into human patients and ethical constraints presently limit human studies. Accordingly, what are needed are novel therapies to treat SLE that are not symptom or tissue specific and novel non-human animal models that translate into human patients to test these novel therapies.

II. SUMMARY

Disclosed are methods and compositions related to novel non-human model animal systems for testing therapeutic agents against systemic lupus erythematosus (SLE).

In one aspect, disclosed herein are non-human animal models for systemic lupus erythematosus (SLE) comprising a severe combined immunodeficient non-human animal comprising exogenous cells from a human subject with SLE.

Also disclosed are non-human animal models of any preceding aspect, wherein the cells from the human subject are peripheral blood mononuclear cells.

In a specific aspect, disclosed herein are non-human animal models of any preceding aspect, wherein the cells from the human subject are adoptively transferred to the severe combined immunodeficient non-human animal such as a rodent (e.g., mouse, rabbit, rat, guinea pig, or hamster), non-human primate, canine, or feline.

Also disclosed herein are methods of screening for a drug candidate that inhibits or reduces SLE through: a) obtaining a tissue sample comprising cells from a subject with SLE, b) contacting the cells with the drug candidate, c) injecting the cells of step b) into a severe combined immunodeficient non-human animal; and d) assaying the immune response to the cells relative to a control, wherein a reduction in one or more immune responses indicates a drug that inhibits or reduces SLE.

In one aspect, disclosed herein are methods of screening of any preceding aspect wherein the control comprises mock or untreated cells.

Also disclosed herein are methods of screening of any preceding aspect wherein the immune responses assayed comprises one or more of the number of T cells, the number of CD4 T cells, the number of CD8 T cells, the number of B cells, the number of NK cells, the percentage of activated CD8 T cells, the percentage of activated CD4 T cells, the expression of IL-10, the expression of IL-12, the expression of IL-2, the expression of IL-6, the expression of IL-13, the expression of IL-4, the expression of IL-8, the expression of IL-1b, the expression of IFN-γ, or the expression of TNF-α.

In one aspect, disclosed herein are microRNA antagonist cocktails comprising any combination of microRNA-21 (SEQ ID NO: 1), microRNA-29a (SEQ ID NO: 2), and/or microRNA-29b (SEQ ID NO: 3). In a specific aspect, disclosed herein are microRNA cocktails further comprising 1,2-Di-(9Z-octadecenoyl)-3-trimethylammonium propane methylsulfate (DOTAP).

Also disclosed herein are method of treating SLE comprising administering to a subject with SLE the microRNA cocktail of any preceding aspect.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, 1C, and 1D show that estrogenic responses are enhanced in SLE and estrogen promotes protein binding to a response element proximal to the STAT1 genetic locus. FIG. 1A shows PBMCs from SLE patients and healthy controls were isolated from whole blood and stimulated with estrogen (E2; 10 nM) for 48 h. RNA was isolated and gene arrays were analyzed using GenePattern software relative to untreated (media) controls. Gray lines indicate a 2-fold change in gene expression with E2 treatment. Black dots indicate probe detection that is not statistically significant; light gray dots and dark gray dots indicate a significant increase or decrease in probe detection, respectively (p b 0.05). FIG. 1B shows the graphical output expressed in reads per million (RPM) of ChIP-enriched DNA sequencing. MCF-7 cells were treated for 45 min with ethanol (EtOH) vehicle or E2 (1 nM) and ChIP assays were performed with ERα specific antibody. Putative ERα binding peak is indicated with an arrow. FIGS. 1C and 1D show EMSA of nuclear lysates from THP-1 cells incubated with 32P-labeled probes corresponding to the ERα binding sequence derived from ChIP-seq (1B). FIG. 1C shows cells stimulated with E2 (10 nM). FIG. 1D shows 6 h incubation with recombinant ERα protein. Representative results are shown from individual experiments run in triplicate (1A) or duplicate (1B, 1C, 1D).

FIGS. 2A, 2B, 2C, and 2D show hormonal regulation of STAT1 expression is specific to estrogen and mediated through estrogen receptor (ER)α. FIG. 2A shows the relative fold change in STAT mRNA expression in human hematopoietically derived cell lines K562 and THP-1 after 48 h estrogen (E2; 10 nM) stimulation compared to untreated (media) controls. FIG. 2B shows the fold change in STAT1 transcript expression in K562 cells over time following treatment with prolactin (PLC), progesterone (PGN), dihydrotestosterone (DHT), or E2 relative to baseline levels. FIGS. 2C and 2D show that THP-1 cells were treated with E2 and transfected with siRNA targeting ERα to measure (2C) ERα or (2D) STAT1 expression by qPCR. Results are expressed as fold changes relative to nonsense (siScramble) controls. Representative results from experiments run in triplicate are shown. *p≤0.05.

FIGS. 3A, 3B, and 3C show that Estrogen stimulates STAT1 expression in primary human cells and is upregulated in SLE. FIGS. 3A and 3B show that PBMCs were stimulated with estrogen (E2; 10 nM) for 48 h. FIG. 3A shows a fold change in STAT1 mRNA expression with E2 treatment relative to untreated (media) controls from SLE patients (n=10) or healthy controls (n=10). FIG. 3B shows a Western blot of total cell lysates from SLE patients (n=3) or healthy controls (n=3). FIG. 3C shows that RNA was isolated from whole blood samples of SLE patients (n=20) and healthy controls (n=10) to measure the relative fold change in STAT1 transcript expression. Reproducible results demonstrated in triplicate. Representative experiments are shown. *p≤0.05.

FIGS. 4A, 4B, 4C, 4D, 4E and 4F show that estrogen-mediated induction of STAT1 regulates TLR8 expression by direct transcriptional activation. THP-1 cells were stimulated with estrogen (E2; 10 nM). FIGS. 4A and 4B show electrophoretic mobility shift assay (EMSA) analysis of nuclear lysates from THP-1 cells with or without E2 treatment for the indicated time. Lysates were incubated with 32P-labeled probes corresponding to a bona fide STAT binding region 24 kb from the 3' end of the of the TLR8 genetic locus. FIG. 4C shows fold change in TLR8 mRNA expression following siRNA (siScramble) transfection relative to untreated (media) controls. FIGS. 4D and 4E show fold change in (4D) STAT1 or (4E) TLR8 transcript expression using siRNA targeting STAT1 (siSTAT1) relative to nonsense siRNA control (siScramble). FIG. 4F shows Western blot of total cell lysates with or without E2 treatment and siRNA-mediated knock down of STAT1 or ERα. Representative experiments are shown from experiments performed in triplicate. *p≤0.05.

FIGS. 5A, 5B, 5C, 5D, and 5E show that miR-21 stimulation induces TLR8 expression and cytokine production. FIG. 5A shows liposome-encapsulated miR-21 or a nonsense control sequence (miR-control) containing a Cy3 fluorescent label conjugate was incubated with THP-1 cells and visualized using fluorescent microscopy. Arrows highlight Cy-3 detection within liposomal vesicles; scale bar=25 μm. Fold change in (5B) TLR8 expression and cytokine secretion of (5C) IL-12 or (5D) IL-13 in THP-1 cells following stimulation with miR-control and miR-21 in liposomal complexes, TLR8 agonist (R-848), miR-21 liposomes+control peptide, or miR-21 liposomes+MyD88 inhibitor peptide. (5E) Primary human macrophages were isolated from healthy blood samples, stimulated with autologous serum, and treated with chemically modified, locked nucleic acid (LNA) sequences of control miR and anti-miR-21, or with chloroquine. Results representative of duplicated experiments. *p≤0.05.

FIGS. 6A, 6B, 6C, 6D, and 6E show that extracellular microRNAs (miRs) are detected primarily within vesicles and liposome encapsulated miR-21 stimulation induces extracellular vesicle (EV) secretion. FIGS. 6A, 6B, and 6C show EV and non-EV fractions were isolated from blood of SLE patients. RNA size and concentration was measured on the Bioanalyzer system. FIG. 6B shows that RNA concentrations of microRNA (miR; 0-40 nt) and small RNA (0-325 nt). Purified intracellular RNA isolated from cells was added to the non-EV fraction as a control (non-EV spike). FIG. 6C shows digital electrophoretic gel image of purified RNA. FIG. 6D shows the extracellular particle profiles and images recorded by nanoparticle tracking analysis from conditioned media collected from THP-1 cells treated with miR control and miR-21 liposomal vesicles or R-848. FIG. 6E shows the area under the curve (0-160 nm) calculations from (6D) made using the linear trapezoidal method. Results duplicated in individual experiments. *p≤0.05.

IV. DETAILED DESCRIPTION

Figure 1A:
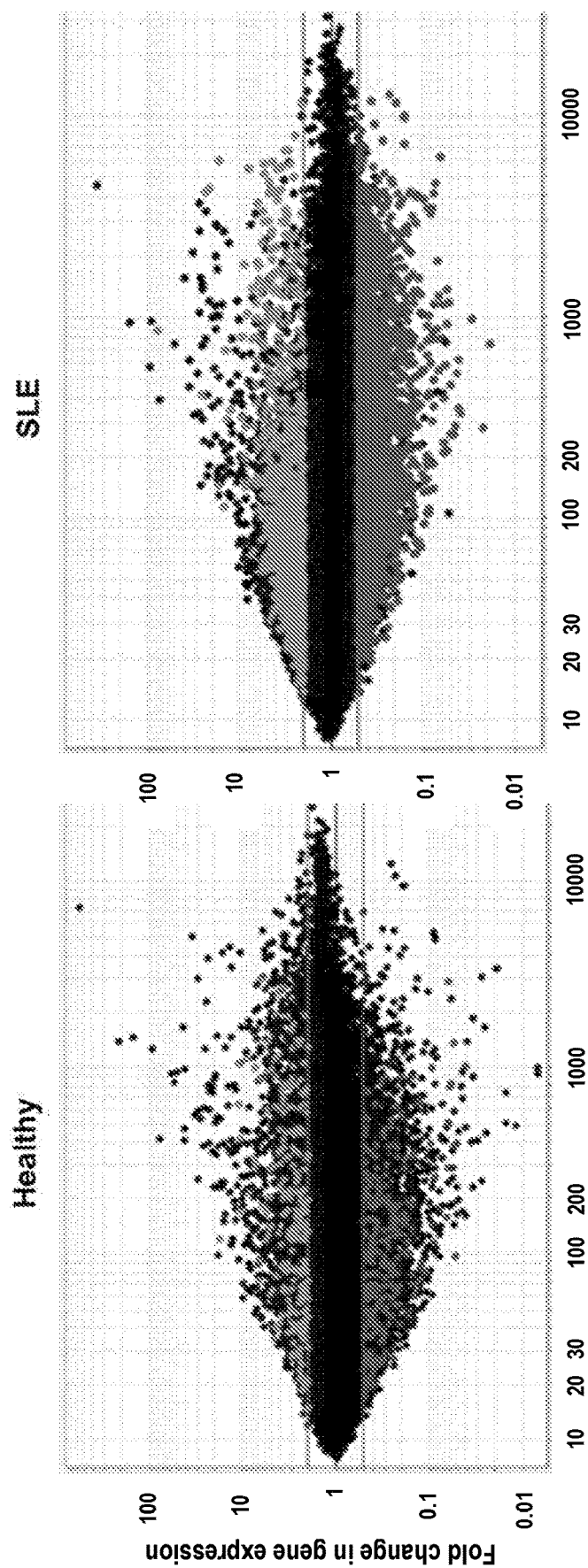

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods and Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular miRNA (such as, for example miR-21, miR-29a, and/or miR-29b) is disclosed and discussed and a number of modifications that can be made to a number of molecules including the miRNA (such as, for example miR-21, miR-29a, and/or miR-29b) are discussed, specifically contemplated is each and every combination and permutation of miRNA (such as, for example miR-21, miR-29a, and/or miR-29b) and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

In one aspect, disclosed herein are non-human animal models for screening novel agents to treat systemic lupus erythematosus (SLE) comprising a non-human animal comprising exogenous cells from a human subject with SLE.

It is understood and herein contemplated that the exogenous cells can be any cell type from the human subject with SLE including, but not limited to peripheral blood mononuclear cells, splenocytes, lymphocytes, neurons, hepatocytes, epidermal cells, monocytes, macrophages, osteoclasts, dendritic cells, and mast cells. In one aspect, it is understood and herein contemplated that it can be both more efficient and provide greater efficacy to utilize a mixture of one or more cell types in the disclosed non-human animal model. Thus, in some aspect, a tissue sample comprising cells can be utilized. Such tissue samples can include, but are not limited to tissue biopsy, whole blood, peripheral blood mononuclear cells, urine sample, lung lavage, sputum, saliva, and fecal sample. Accordingly, in one aspect, disclosed are non-human animal models comprising exogenous cells from a human subject with SLE, wherein the cells from the human subject are peripheral blood mononuclear cells.

In a specific aspect, the non-human animal for use in the disclosed models for screening for novel agents to treat systemic lupus erythematosus can be any species of non-human animal where such screens can be conducted including but not limited to rodents (e.g., mouse, rabbit, rat, guinea pig, or hamster), non-human primate, canine, or feline. In one aspect, the non-human animal can be genetically engineered to be deficient in one or more components of the innate or adaptive immune system in the animal. For example, the animal can be genetically engineered to be deficient in CD4 T cells, CD8 T cells, B cells, NK cells, and/or macrophages. In one aspect, the non-human animal can be a severely compromised immunodeficient rat or mouse, such as, for example, a NOD scid gamma (e.g., NOD.Cg-Prkdcscid Il2rgtm1Wj1/SzJ; NSG) mouse. Accordingly, in one aspect, disclosed herein are non-human animal models for screening novel agents to treat SLE comprising a severe combined immunodeficient non-human animal comprising exogenous cells from a human subject with SLE, wherein the non-human animal is a NOD.Cg-Prkdcscid Il2rgtm1Wj1/SzJ (NSG) mouse.

It is understood and herein contemplated that the disclosed chimeric non-human animals (i.e., severe compromised immunodeficient non-human animal comprising exogenous cells from a human with SLE) disclosed herein can be used to screen for drug candidates that modulate the immune response in SLE thereby treating SLE. Accordingly, in one aspect, disclosed herein are methods of screening for a drug candidate the inhibits or reduces SLE comprising: a) obtaining a tissue sample comprising cells from a subject with SLE, b) contacting the cells from the tissue sample with the drug candidate, c) injecting the cells of step b into a severe combined immunodeficient non-human animal; and d) assaying the immune response to the cells relative to a control; wherein a reduction in one or more immune responses indicates a drug that inhibits or reduces SLE.

It is understood and herein contemplated that the agents screened in the disclosed screening methods can be any agent that may provide a therapeutic benefit to a subject with SLE. For example, the agent can be an antibody, small molecule, nucleic acid (for example RNA, DNA, cDNA, miRNA (such as, for example, miR-21, miR-29a, and miR-29b), siRNA, mimic, aptomer, or other functional nucleic acid), peptide, or protein.

Controls can be important in the disclosed methods as the presence of the control provides a basis to determine if the treatment had an effect. In one aspect, controls can be positive or negative controls. Controls can include subject receiving untreated cells, mock treated cells (such as, for example, cells receiving vector/vehicle alone, a defective agent (such as an miRNA with a nonsense/scrambled sequence (for example miRScramble)) a random antibody, or a placebo small molecule. Therefore, in one aspect, disclosed herein are methods of screening wherein the control comprises mock or untreated cells.

1. Immunoassays and Fluorochromes

It is understood and herein contemplated that the agents being screened for treatment of SLE can modulate immune responses and can derive their functionality through said modulation. The modulation of immune responses allows for evaluation of the efficacy of the agent to come via measurement of immune responses following contact with the agent. Accordingly, disclosed herein are methods of screening of any preceding aspect wherein the immune responses assayed comprises one or more of the number of T cells: the number of CD4 T cells, the number of CD8 T cells, the number of B cells, the number of NK cells, the percentage of activated CD8 T cells, the percentage of activated CD4 T cells, the expression of IL-10, the expression of IL-12, the expression of IL-2, the expression of IL-6, the expression of IL-13, the expression of IL-4, the expression of IL-8, the expression of IL-1b, the expression of IFN-γ, or the expression of TNF-α.

Measurement of immune responses can occur by any means known in the art. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange: Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer: DiD (DilC 18(5)); DIDS; Dihydrorhodamine 123 (DHR); DiI (DilC 18(3)); I Dinitrophenol; DiO (DiOC 18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; FluoroGold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-1 PRO-3; Primuline; Procion Yellow; Propidium Iodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine; Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance; i.e., where the substance can be found in a subject, tissue, or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in a hemagglutination assay) or very small particles (as in latex an agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field, on the net charge, size and shape of the molecules, and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein, incorporated by reference in its entirety for its teaching regarding two-dimensional electrophoresis methods. Other examples include, but are not limited to: Anderson, L and Anderson, NG, High resolution two-dimensional electrophoresis of human plasma proteins, Proc. Natl. Acad. Sci. 74:5421-5425 (1977); and Ornstein, L., Disc electrophoresis, L. Ann. N.Y. Acad. Sci. 121:321349 (1964). Each of which is herein incorporated by reference in its entirety for teachings regarding electrophoresis methods. Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. For example, standard methods for Western blot analysis can be found in: D. M. Bollag et al., *Protein Methods* (2d edition 1996); and E. Harlow & D. Lane, *Antibodies, a Laboratory Manual* (1988), U.S. Pat. No. 4,452,901. Each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to the remaining surface area on the nitrocellulose to prevent non-specific detection. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}I$). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in: Ornstein L., Disc electrophoresis—I: Background and theory, Ann. NY Acad. Sci. 121:321-349 (1964); and Matsudiara, PT and DR Burgess, SDS microslab linear gradient polyacrylamide gel electrophoresis, Anal. Biochem. 87:386-396 (1987). Each of which is herein incorporated by reference in its entirety for teachings regarding gel-shift assays.

In a general gel-shift assay, purified proteins or crude cell extracts can be incubated with a labeled (e.g., $^{32}P$-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{111}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase, and acetylcholinesterase.

Variations of ELISA techniques are known to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a secondary antibody specific for the target protein, which is linked to a detectable label. This type of ELISA is a simple "sandwich ELISA." Detection also can be achieved by the addition of a secondary antibody, followed by the addition of a tertiary antibody that has binding affinity for the secondary antibody, with the tertiaryantibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled tertiary binding agent.

Enzyme-Linked Immunospot Assay (ELISPOT) is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, 3-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase, and acetylcholinesterase. In this assay, a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the secondary or tertiary antibody can have an associated label to allow detection, as described above. This can be an enzyme that can generate color development upon incubating with an appropriate chromogenic substrate. Thus, for example, one can contact and incubate the primary or secondary immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies, and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, NJ) and specialized chip designs, such as engineered microchannels in a plate (e.g., The Living Chip™, Biotrove, Woburn, MA) and tiny 3D posts on a silicon surface (Zyomyx, Hayward CA). Particles in suspension can also be used as the basis of arrays, providing they are coded for identification; systems include color coding for microbeads (Luminex, Austin, TX; Bio-Rad Laboratories) and semiconductor nanocrystals (e.g., QDots™, Quantum Dot, Hayward, CA), and barcoding for beads (UltraPlex™, SmartBead Technologies Ltd, Babraham, Cambridge, UK) and multimetal microrods (e.g., Nanobarcodes™ particles, Nanoplex Technologies, Mountain View, CA). Beads can also be assembled into planar arrays on semiconductor chips (LEAPS technology, BioArray Solutions, Warren, NJ).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and both reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, WA) reversible covalent coupling is achieved by interaction between the protein derivatised with phenyldiboronic acid and salicylhydroxamic acid immobilized on the support surface. This has low background binding, low intrinsic fluorescence, and allows the immobilized proteins to retain function. Noncovalent binding of unmodified protein occurs within porous structures such as HydroGel™ (PerkinElmer, Wellesley, MA), which is based on a 3-dimensional polyacrylamide gel; this substrate is reported to give a particularly low background on glass microarrays with a high capacity and retention of protein function. Widely used biological coupling methods are through biotin/streptavidin or hexahistidine/Ni interactions, having modified the protein appropriately. Biotin may be conjugated to a poly-lysine backbone immobilized on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA; PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, AZ), rolling circle DNA amplification (Molecular Staging, New Haven CT), mass spectrometry (Intrinsic Bioprobes; Ciphergen, Fremont, CA), resonance light scattering (Genicon Sciences, San Diego, CA) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides, or nucleic acid aptamers, which bind and detect specific target ligands in high throughput manner.

Antibody arrays have the required properties of specificity and acceptable background and some are available commercially (BD Biosciences, San Jose, CA; Clontech, Mountain View, CA; BioRad; Sigma, St. Louis, MO). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; Biolnvent, Lund, Sweden; Affitech, Walnut Creek, CA; Biosite, San Diego, CA). In addition to the conventional antibodies, Fab and scFv fragments, single V-domains from camelids, or engineered human equivalents (Domantis, Waltham, MA) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staphylococcus aureus* protein A (Affibody, Bromma, Sweden), 'Trinectins' based on fibronectins (Phylos, Lexington, MA), and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, CO). Aptamers may be selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance, and atomic force microscopy, avoid alteration of ligand. What is required from any method is optimal sensitivity and specificity, with low background to give high signal to noise ratios. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, CA).

Another methodology which can be used diagnostically and in expression profiling is the ProteinChip® array (Ciphergen, Fremont, CA), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, CT).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

2. Novel miRNAs and Methods of Treating SLE

Throughout the present disclosure, miRNA antagonists were created that have a beneficial effect in treating SLE. Thus, in one aspect, disclosed herein are microRNA antagonists anti-miR-21 (SEQ ID NO: 1), anti-miR-29a (SEQ ID NO: 2), and/or anti-miR-29b (SEQ ID NO; 3). In one aspect, any one or any combination of two, three, or more of the miRNA antagonists can be formulated as a cocktail to administer to a subject. Accordingly, disclosed herein are miRNA antagonist cocktails comprising any one or combination of anti-miR-21 (SEQ ID NO: 1), anti-miR-29a (SEQ ID NO: 2), and/or anti-miR-29b (SEQ ID NO: 3). The disclosed cocktails can be further modified to comprise a polar lipid. Thus, in a specific aspect, disclosed herein are microRNA cocktails further comprising 1,2-Di-(9Z-octadecenoyl)-3-trimethylammonium propane methylsulfate (DOTAP).

It is understood and herein contemplated that the miRNAs disclosed herein can be used to treat or inhibit SLE. Accordingly in one aspect, disclosed herein are methods of treating or inhibiting SLE comprising the administration of any microRNA antagonist (such as, for example, anti-miR-21, anti-miR-29a, and/or anti-miR-29b), combination of microRNA antagonists, or cocktail thereof disclosed herein to a subject with SLE. For example, in one aspect, disclosed herein are methods of treating SLE comprising administering to a subject with SLE one or more of anti-miR-21 (SEQ ID NO: 1), anti-miR-29a (SEQ ID NO: 2), and/or anti-miR-29b (SEQ ID NO: 3).

3. Nucleic Acids

There are a variety of molecules disclosed herein that are nucleic acid based, including for example the nucleic acids that encode, for example miRNA (such as, for example miR-21, miR-29a, and/or miR-29b), or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the anti sense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenine (A), cytosine (C), guanine-9-yl (G), uracil (U), and thymine (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, Ni, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of any of the disclosed nucleic acids or the genomic DNA of any of the disclosed nucleic acids, or they can interact with the polypeptide encoded by any of the disclosed nucleic acids. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNaseH mediated RNA-DNA hybrid degradation. Alternatively, the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of anti sense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with a $k_d$ from the target molecule of less than 10.12 M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. Representative examples of how to make and use aptamers to bind a variety of different target molecules can be found in the following non-limiting list of U.S. Pat. Nos. 5,476,766, 5,503,978, 5,631,146, 5,731,424, 5,780, 228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions, which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci. USA* 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

4. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

5. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue: Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129.57-80, (1992); and Roffler, et al., *Biochem. Pharmacol,* 42:2062-2065, (1991). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue: Hughes et al., *Cancer Research,* 49:6214-6220, (1989); and Litzinger and Huang, *Biochimica et Biophysica Acta,* 1104:179-187, (1992). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, NJ, (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

6. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers, such as cationic liposomes. Appropriate means for transfection, including viral vectors, chemical transfectants, or physico-mechanical methods such as electroporation and direct diffusion of DNA, are described by, for example, Wolff, J. A., et al., *Science*, 247, 1465-1468, (1990); and Wolff, J. A. *Nature*, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

The disclosed anti-miR21, anti-miR-29a, and/or anti-miR-29b, can be transported into a cell as a liposomal vector or naked nucleic acid. Nevertheless, the anti-miRs disclosed herein can also be incorporated into a larger plasmid, viral vectors, liposomal complexes. As used herein plasmid, viral vectors, or liposomal complexes are agents that can transport the disclosed nucleic acids, such as anti-miR-21, anti-miR-29a, and/or anti-miR-29b into the cell without degradation. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred as vectors are any viral families which share the properties of these viruses, which make them suitable for use. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transfection efficiencies (ability to introduce genes) than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms.

A retrovirus is essentially a package which has packed into it nucleic acid cargo in the form of RNA. The nucleic acid cargo carries with it a packaging signal, which ensures that the replicated daughter molecules will be efficiently packaged within the package coat. In addition to the package signal, there are a number of molecules which are needed for the replication and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription (including a primer binding site to bind the tRNA primer of reverse transcription), terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles by the machinery provided in cis by the helper cell.

(2) Adenoviral Vectors

The construction of replication-defective adenoviruses has been described: Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); and Zhang et al. *BioTechniques* 15:868-872 (1993). The benefit of the use of these viruses as vectors is that they are limited in the extent to which they can spread to other cell types, since they can replicate within an initial infected cell, but are unable to form new infectious viral particles. Recombinant adenoviruses have been shown to achieve high transfection efficiency after direct, in vivo delivery to airway epithelium, hepatocytes, vascular endothelium, CNS parenchyma, and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267: 25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993). Recombinant adenoviruses achieve gene transduction by binding to specific cell surface receptors, after which the virus is internalized by receptor-mediated endocytosis, in the same manner as wild type or replication-defective adenovirus: Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); and Wickham et al., *Cell* 73:309-319 (1993).

A viral vector can also be one based on an adenovirus which has had the E1 gene removed and these virons are generated in a cell line such as the human 293 cell line. In another preferred embodiment, both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, CA, which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs), which flank at least one cassette containing a promoter that directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide nucleic acid molecules, which are capable of delivery into mammalian cells in vitro and in vivo.

The inserted genes in viral and retroviral usually may contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular experiments with large human herpesviruses have provided a means whereby large heterologous DNA fragments can be cloned, propagated, and established in cells permissive for infection with herpesviruses (Sun et al., *Nature genetics* 8: 33-41, 1994; Cotter and Robertson, *Curr Opin Mol Ther* 5: 633-644, 1999). These large DNA viruses (herpes simplex virus (HSV) and Epstein-Barr virus (EBV) for instance, have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, which is constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed anti-miR-21, anti-miR-29a, and/or anti-miR-29b or vectors for example, lipids such as liposomes, such as cationic liposomes (e.g., DOTMA, DOPE, DC-cholesterol, and/or DOTAP) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Natl. Acad. Sci LISA* 84:7413-7417 (1987); and U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous nucleic acids into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, MD), SUPERFECT (Qiagen, Inc. Hilden, Germany) and TRANSFECTAM (Promega Biotec, Inc., Madison, WI), as well as other liposomes developed according to procedures standard in the art. In addition, the disclosed nucleic acid or vector can be delivered in vivo by electroporation, the technology for which is available from Genetronics, Inc. (San Diego, CA) as well as by means of a SONOPORATION machine (ImaRx Pharmaceutical Corp., Tucson, AZ).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of nucleic acids through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

7. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)).

Enhancer generally refers to a sequence of DNA that functions at no fixed distance from the transcription start site and can be either 5' (Laimins, L. et al., *Proc. Natl. Acad Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4; 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs, the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. For instance, the glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

8. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, the kit could be designed to screen for agents that treat SLE and include any one or more anit-miR-21, anti-miR-29a, anti-miR-29b: a control miRNA such as miR scramble, a vector control, and/or PBMC or other cells from a subject with SLE, or any combination thereof.

C. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook el al., *Molecular Cloning: A Laboratory Mlanual*, 2nd Edition (Cold Spring Harbor Laboratory Press, Cold Spring Harbor, NY, 1989) Chapters 5, 6) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, MA or ABI Model 380B). Synthetic methods useful for making oligonucleotides are also described by Ikuta et al., *Ann. Rev. Biochem.* 53:323-356 (1984) (phosphotriester and phosphite-triester methods), and Narang et al., *Method Enzymol.*, 65:610-620 (1980), (phosphotriester method). Protein-containing nucleic acid molecules can be made using known methods such as those described by Nielsen et al., *Bioconjug. Chem.* 5:3-7 (1994).

2. Process Claims for Making the Compositions

Disclosed are processes for making the compositions as well as making the intermediates leading to the compositions. For example, disclosed are nucleic acids in SEQ ID NOs: 1, SEQ ID NO: 2, and/or SEQ ID NO: 3. There are a variety of methods that can be used for making these compositions, such as synthetic chemical methods and standard molecular biology methods. It is understood that the methods of making these and the other disclosed compositions are specifically disclosed.

Also disclosed are nucleic acid molecules produced by the process comprising linking in an operative way a nucleic acid molecule comprising a sequence having 80% identity to a sequence set forth in SEQ ID NOs: 1, SEQ ID NO: 2, and/or SEQ ID NO: 3.

Disclosed are nucleic acid molecules produced by the process comprising linking in an operative way a nucleic acid molecule comprising a sequence that hybridizes under stringent hybridization conditions to a sequence set forth SEQ ID NOs: 1, SEQ ID NO: 2, and/or SEQ ID NO: 3 and a sequence controlling the expression of the nucleic acid.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Estrogen-Regulated STAT1 Activation Promotes TLR8 Expression to Facilitate Signaling Via microRNA-21 in Systemic Lupus Erythematosus Estrogen can promote gene expression by several mechanisms, but the primary route of influence is the classical pathway, which is mediated by direct DNA binding of cytosolic estrogen receptors alpha and beta (ERα/β) to estrogen response elements (EREs) following nuclear translocation. While a limited number of genes are known to be regulated by estrogen at present, recent evidence suggests that this list is likely much larger. In lupus mouse models, studies have shown enhanced survival and decreased disease severity with ERα deficiency, while no effect was observed with regard to ERβ; thus supporting other studies also indicating the important role of the ERα receptor subtype in promoting autoimmune-mediated inflammation. Additionally, identified herein is a novel ERE proximal to the Toll-like receptor (TLR)8 genetic locus and, using peripheral blood mononuclear cells (PBMCs) derived from systemic lupus erythematosus (SLE) patients and healthy controls, herein it is demonstrated both elevated expression of TLR8 in SLE and significant ERα-dependent induction with estrogen treatment. Furthermore, stimulation of leukocytes from ERα deficient, lupus-prone mice with TLR agonists has been shown to elicit a significantly reduced inflammatory response. Collectively, these data indicate an association between ERα-mediated TLR activation following estrogen stimulation and suggest that this pathway can be involved pathologically in SLE.

TLR8 is an innate immune system receptor expressed predominately in macrophages that stimulates inflammatory responses by binding to pathogen-associated, single-stranded (ss) RNA sequences. Despite the well-established association of the adaptive arm of the immune system, the role of innate immunity in SLE pathogenesis and perpetuation has recently emerged. TLRs serve as a key interface between innate and adaptive immunity and can therefore be a mechanistic link between these responses. Synthetic agonist stimulation of TLR8 expression is enhanced in the presence of estrogen and heightened in females when compared to male counterparts, which indicates that estrogen can lower the threshold of inflammatory activation in the presence of a TLR8 agonist and produce a sex-biased response. In addition to synthetic and viral ssRNA agonists, recent cancer research has uncovered that endogenous microRNAs (miRs) can also mediate paracrine TLR8 activation. These results demonstrated that extracellular vesicles (EVs) containing miR-21 secreted from tumor cells were engulfed by macrophages, fused with endosomes, and activated pro-inflammatory cytokine expression via TLR8 binding and signaling.

Since EVs are associated with inflammation and distinct miR expression patterns have been characterized in SLE, this TLR8 signaling pathway can present a novel sex-biased mechanism regulating autoimmunity. To examine estrogen signaling and TLR8 activation in SLE, primary human cells and cell lines were treated with estrogen. Enhanced estrogenic responses were observed in SLE patients and identify a putative ERE for ERα to promote signal transducer and activator of transcription (STAT)1 expression. Furthermore, STAT1 transcriptionally regulates TLR8 expression and is overexpressed in SLE patients. To investigate miR-21 as an endogenous agonist to mediate TLR8 activation, liposomal formulations containing miR-21 were used to stimulate TLR8 and cytokine expression; conversely, this response was suppressed in primary macrophages with a miR-21 antagonist. Taken together, these data indicate that estrogen can stimulate TLR8 expression either directly through an ERE or indirectly through STAT1 and can be activated by EV-derived miR-21, which presents a novel therapeutic pathway to target in SLE.

a) Materials and Methods
(1) Human Samples

Female SLE patients meeting the revised criteria of the American College of Rheumatology were recruited for this study from The Ohio State University Wexner Medical Center (OSUWMC) clinics. Age and sex-matched healthy volunteers were recruited from the American Red Cross and local communities using the Research Match program through the Center for Clinical and Translational Science (CCTS) at The Ohio State University. All study participants were not taking hormonal medications and were pre-menopausal. Participation was in accordance with an approved Institutional Review Board protocol at OSUWMC. Samples obtained for processing were either whole blood collected into heparinized tubes or filtered blood samples. PBMC isolation was carried out using Ficoll-Paque centrifugation (GE Healthcare, Uppsala, Sweden).

(2) Gene Arrays

Total RNA was submitted for gene array analysis using HG-U133 AFFYMETRIX® Human Gene Chips with untreated PBMC arrays serving as the internal baseline control for each individual sample. Baseline values were subtracted from the estrogen-treated expression values, thus, only the estrogen-mediated effect was reported. Plots were generated using the Multiplot function within the GenePattern software program and the data was analyzed using the core Analysis function of Ingenuity Pathway Analysis Software as detailed formerly.

(3) Hormone Treatment

Human PBMCs were isolated from patients and cultured in hormone free conditions using RPMI 1640 (Life Technologies, Grand Island, NY) and 5% charcoal stripped fetal bovine serum (FBS; Life Technologies). Hematopoietic cell lines were grown in RPMI 1640 supplemented with 10% FBS then transferred to XVIVO-15 (Lonza, Basel, Switzerland) chemically defined, hormone free media for 24 h prior to hormone stimulation. Cells were treated with 10 nM of 17β-estradiol (E2; Sigma-Aldrich, St. Louis, MO), 10 nM progesterone (Sigma), 10 ng/mL prolactin (Sigma), or 10 nM dihydrotestosterone (5α-androstatin-17β-ol-one; Fluka, Buchs, Switzerland) and were collected at the indicated times.

(4) Chromatin Immunoprecipitation Sequencing (ChIP-Seq)

MCF-7 cells were treated with 1 nM E2 for 45 min following 72 h culture in DMEM (Life Technologies) media containing 5% charcoal/dextran treated FBS. ChIP assays were performed using ERα antibody (Santa Cruz Biotechnology, Santa Cruz, CA). Sequencing libraries were prepared from ChIP enriched DNA using the Tru-seq Chip Sample Prep Kit (Illumina, San Diego, CA) according to the manufacturer's protocol. Each library was sequenced on one lane of an Illumina GA IIx platform generating 40 bp single end reads. Sequences were aligned to the University of California, Santa Cruz hg19 human reference genome using the Bowtie short read mapping utility and graphical maps of aligned reads were generated using HOMER. Images shown were generated in the Integrative Genomics Viewer.

(5) RNA Purification and qPCR

Cellular RNA was isolated, quantitated, synthesized to cDNA, and used for quantitative (q) PCR. Briefly, RNA was isolated from PBMCs using the RNeasy Mini Kit (Qiagen Sciences, Valencia, CA) and from whole blood samples using the Paxgene Blood RNA Kit (PreAnalytix; Qiagen) according to the manufacturer's protocol. RNA was quantitated using a NanoDrop 1000 spectrophotometer (NanoDrop Products, Wilmington, DE). cDNA was synthesized using High Capacity cDNA Reverse Transcription Kit (Applied Biosystems, Foster City, CA) following the manufacturer's protocol and qPCR was performed using the TaqMan system (Applied Biosystems) using cDNA and gene specific primers in accordance with the manufacturer's protocol. All samples were run on the ABI Prism 7900HT Sequence Detection System (Applied Biosystems) and normalized to 18sRNA as an internal positive control. Results were analyzed using the 2-ΔΔCt method.

For analysis of RNA in EVs, RNA was isolated according to the manufacturer's protocol using the MagMAXmirVana total RNA isolation kit (Thermo Fisher Scientific, Rockford, IL). EVs were isolated per manufacturer's protocol from human serum using ExoQuick (System Biosciences, Palo Alto, CA). Both the EV and non-EV fractions were processed in the presence of chemical RNase inhibitor, RNAsecure (Thermo Fisher Scientific). Purified RNA was measured on the Agilent 2100 bioanalyzer system using the Total RNA Pico and Small RNA capillary electrophoresis assays (Agilent Technologies, Santa Clara, CA).

(6) Electrophoretic Mobility Shift Assay (EMSA)

EMSA was performed as detailed formerly. Briefly, cells were stimulated with 10 nM E2 (Sigma) for the indicated time and nuclear lysates were incubated with probes labeled with [32P] dCTP by the Klenow fragment of DNA polymerase. Probes corresponding to the putative ERE site proximal to the STAT1 genetic locus included: 5'-GG-GAGAATCTAGGTCAAGGTCCTTC-3' (SEQ ID NO; 4) and 5'-GAAGGACCTTGACCTAGATTCT-3' (SEQ ID NO: 5). Additionally, recombinant ERα protein (ThermoScientific) was incubated with these DNA fragments to confirm the specificity prior to gel electrophoresis. Probes designed to interrogate a previously characterized STAT1 binding region downstream of the TLR8 genetic locus included: 5'-GGGCTTTATTCTCTGAAACACCCACT (SEQ ID NO: 6) and 5'-AGTGGGTGTTTCAGAGAATAAAG (SEQ ID NO: 7).

(7) Western Blotting

Samples were prepared and western blotting was performed. Briefly, cell lysates were prepared using Bio-Rad Sample buffer (Life Science Research, Hercules, CA) containing 0.5% 2-mercaptoethanol. Protein samples were resolved on 4-20% Tris-HCl Bio-Rad Ready Gels (Life Science Research) and transferred onto PVDF membranes (GE Healthcare). Membranes were incubated with TLR8 (Rockland Immunochemicals Inc., Gilbertsvilla, PA), STAT1 (Santa Cruz Biotechnology), or p-STAT1 (Santa Cruz Biotechnology) antibody and stripped using Millipore Re-Blot Plus (Millipore, Temecula, CA) for reprobing with monoclonal β-actin antibody (Sigma Aldrich). ImageJ software (NIH, Bethesda, MD, v1.45s) was used to measure signal intensities and results were analyzed with Microsoft Excel (v2013). Final quantitations of protein expression were determined by normalization to 3-actin levels.

(8) Liposomal Transfection and Fluorescent Microscopy

Cells were stimulated with synthetically produced vesicles containing miR-21 by encapsulating 15 μg of miR-21 mimic 5'-UAGCUUAUCAGACUGAUGUUGA-3' (SEQ ID NO: 8) (Sigma) or miR-scramble 5'-UAAGGC-UAUGAAGAGAUAC-3' (SEQ ID NO: 9) (Sigma) using DOTAP (Roche, Basel, Switzerland) transfection reagent according to the manufacturer's protocol. Fluorescent microscopy was captured on the ZOE fluorescent cell imager (Bio-Rad) using smart-flare miR-21 (EMD Millipore Bioscience, Billerica, MA) or miR-scramble (EMD) in RNAi-MAXX Lipofectamine reagent (ThermoFisher) following the manufacturer's protocol. Cells were treated with 0.3 μg/mL R-848 (Enzolife Sciences, Farmingdale, NY), 100 μM of MyD88 inhibitor (Novus Biologicals, Littleton, CO), or 100 μM of control peptide (Novus Biologicals) as indicated. After 24 h, cells and supernatants were collected. To target autologous EVs containing miR-21, primary human PBMCs were isolated from whole blood as indicated above, incubated in the presence of 20% autogolous serum, and treated with locked nucleic acid (LNA) sequences designed to antagonize miR-21 (Exiqon, Vedbaek, Denmark) following liposomal complexing with DOTAP (Roche) according to the manufacturer's protocol.

(9) ELISA (Enzyme-Linked Immunosorbent Assay)

Analysis of cytokine expression was performed on conditioned media using electrochemiluminescence detection (Meso Scale Diagnostics, Rockville MD) according to the manufacturer's protocol and data was analyzed using Microsoft Excel (v2013).

(10) Nanoparticle Tracking Analysis (NTA)

The NanoSight LM 10 system (NanoSight, Wiltshire, United Kingdom) was used to measure the rate of Brownian motion of particles to determine the size and quantification of EVs. Briefly, the sample was injected in a NanoSight cubicle and the size of particles was obtained by determining the motion in fluid passing across the chamber. The number of particles per milliliter was measured from a 0-160 nm range and was acquired from both experimental and control samples for comparison using area under the curve calculations obtained via the linear trapezoidal analysis method.

(11) Statistics

All numerical data were expressed as mean values±standard deviation. Statistical differences were determined by paired, two-tailed, Student t-tests using Microsoft Excel (v2013) and considered statistically significant if p≤0.05.

b) Results (1) Heightened Estrogenic Responses are Observed in SLE Patients

Physiological levels of estrogen can effectively lower the threshold of immune activation, which can account for enhanced resistance to infectious disease in many female species, but can also contribute to autoimmunity if dysregulated. Using PBMCs derived from SLE patients or age and sex-matched healthy controls, microarray gene expression data was used to identify potential genes regulated by estrogen to account for this response. To further explore estrogenic potential to influence genetic expression genome-wide in PBMCs from both SLE patients and healthy individuals, this gene array data was analyzed using GenePattern software. Using the Multiplot function within the program to create a 2-parameter scatter plot, the genome-wide estrogenic effect on the entire probe set can visualized simultaneously. With estrogen treatment of healthy PBMCs, 236 probes are significantly upregulated over 2-fold and 244 are downregulated more than 2-fold (p≤0.05; FIG. 1A). However, the response with estrogen stimulation of SLE PBMCs was heightened; here, 1005 and 2530 probes are significantly up or downregulated over 2-fold, respectively (p≤0.05; FIG. 1A). To identify genes that are uniquely regulated with estrogen treatment in both healthy and SLE samples, expression values were plotted onto a fold change vs. fold change plot. If expression is regulated similarly in healthy and SLE datasets on this plot, the probe will follow a linear relationship and appear in the upper-right or lower-left quadrants. Conversely, exclusive up and downregulation will appear in the remaining quadrants. While estrogen treatment exclusively upregulated 134 and downregulated 107 probes in healthy volunteers, 525 and 1629 were significantly up or downregulated in SLE patients to statistical significance, respectively. These results were consistent with an enhanced responsiveness to estrogen in SLE patients.

(2) Putative Estrogen Response Element is Identified Proximal to STAT1

Figures 1B, 1C:
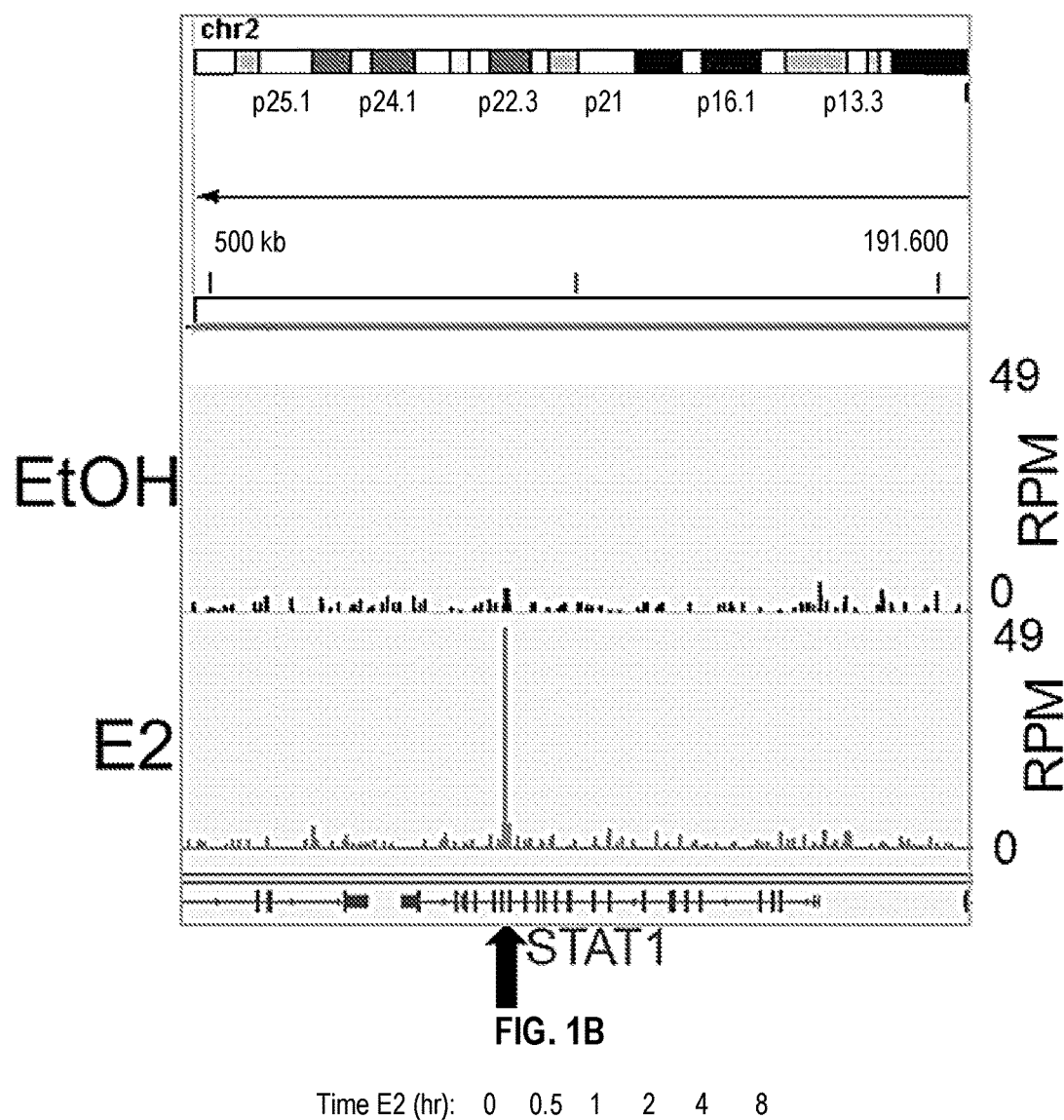

To further validate the array data and identify candidate genes potentially regulated by ERα in SLE, chromatin immunoprecipitation sequencing (ChIP-seq) was performed on a human breast cancer cell line (MCF-7) stimulated with a physiological dose of estrogen for 45 min. Following stimulation, nuclear extracts were cross-linked and incubated with ERα antibody to identify putative EREs. Chip-seq analysis revealed a novel intragenic binding peak within the STAT1 genetic locus with estrogen treatment (FIG. 1B). STAT1 regulates the induction of interferon stimulated gene expression and has recently been identified to play a key role in autoimmune disease, including rheumatoid arthritis, diabetes, and inflammatory bowel disease. Furthermore, while a previous study has demonstrated induction of STAT expression and activation in a murine model of lupus nephritis, human data displaying this association is currently lacking and the role of this signaling pathway in SLE pathogenesis has yet to be comprehensively characterized.

Figure 1D:
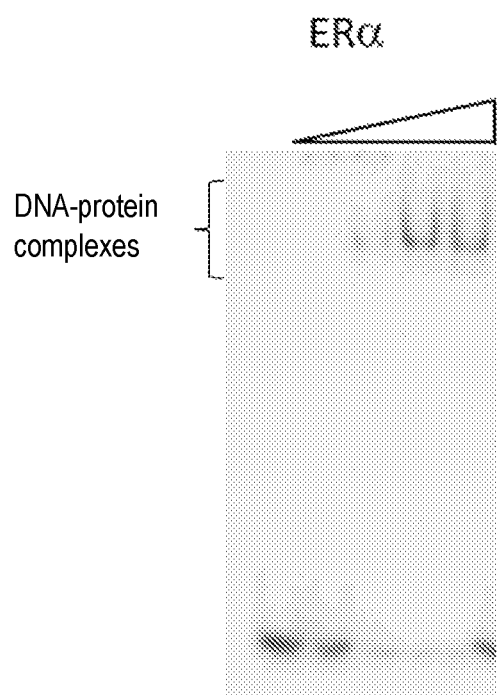

To confirm estrogen-mediated DNA-protein complex formation using this putative ERE sequence intragenic to STAT1, an electrophoretic mobility shift assay (EMSA) was performed using the human macrophage precursor THP-1 monocytic cell line after estrogen stimulation. Nuclear extracts were collected longitudinally and incubated with radiolabeled probes containing the STAT1 ERE sequence. Enhanced DNA-protein complex formation is observed following estrogen stimulation at both the 1 h and 2 h time points and the signal gradually declines following longer incubations (FIG. 1C). To demonstrate binding specificity to this putative ERE, recombinant ERα protein was used because ERα forms transcriptional complexes, which have the potential to mask epitopes in supershift assays. When incubated with radiolabeled probes containing the STAT1 ERE sequences identified above, dose dependent enhancement of DNA-protein complex formation is observed (FIG. 1D).

(3) Estrogen Stimulation of STAT1 Expression Occurs Via ERα

Figure 2A:
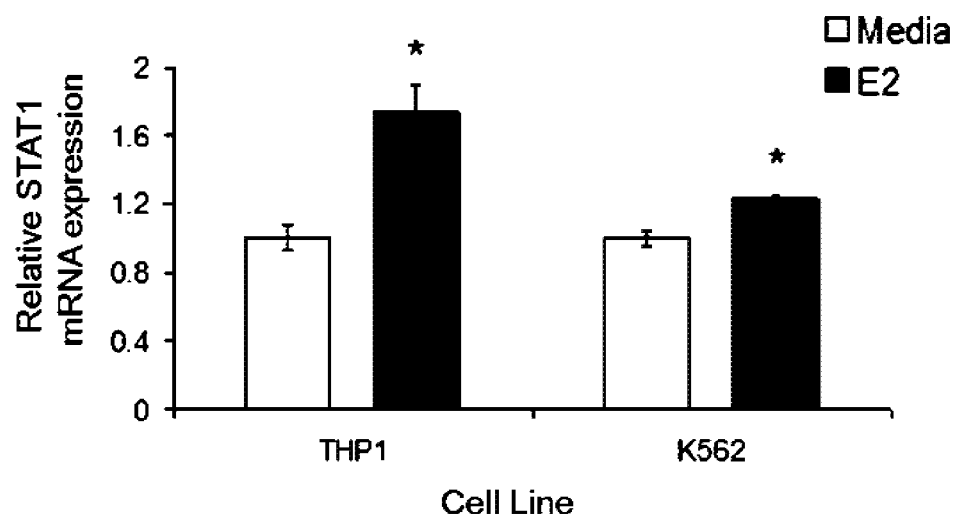
Figure 2B:
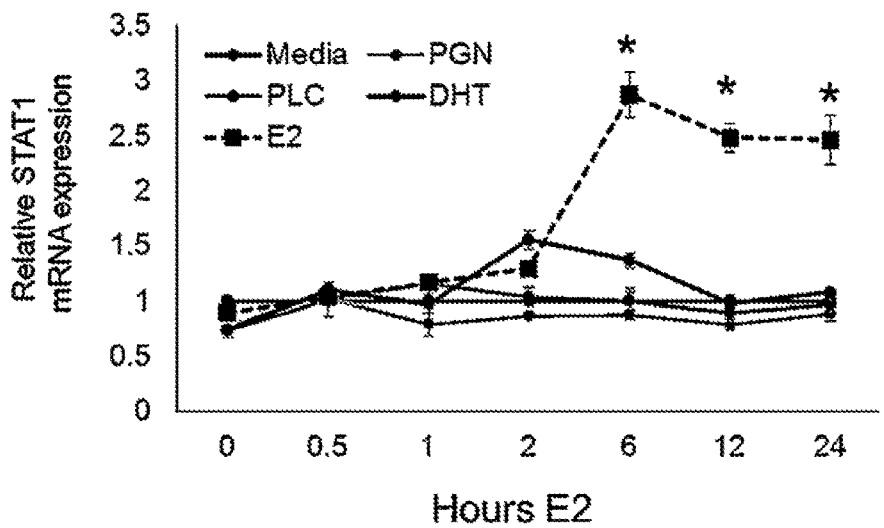

To evaluate the induction of STAT1 expression in hematopoietically derived cell lines with estrogen treatment, THP-1 and K562 cells were stimulated with estrogen for 24 h. Relative to untreated cells, estrogen significantly upregulated STAT1 mRNA transcript expression in THP-1 and K562 cells 1.7-fold ($p \leq 0.01$) and 1.25-fold ($p \leq 0.01$), respectively (FIG. 2A). Using separate treatments of prolactin, progesterone, dihydrotestosterone, or estrogen, the induction of STAT1 expression in THP-1 cells was further analyzed. The results show that hormonal influence was only observed with estrogen treatment when normalized to untreated cells, here, statistically significant ($p \leq 0.01$) induction of STAT1 transcript expression was observed as early as 6 h and continued to remain elevated over 2-fold up to the 24 h time point (FIG. 2B).

Figure 2C:
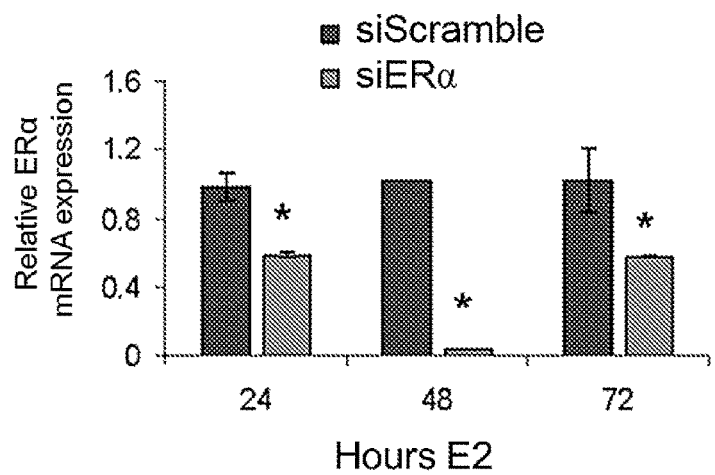
Figure 2D:
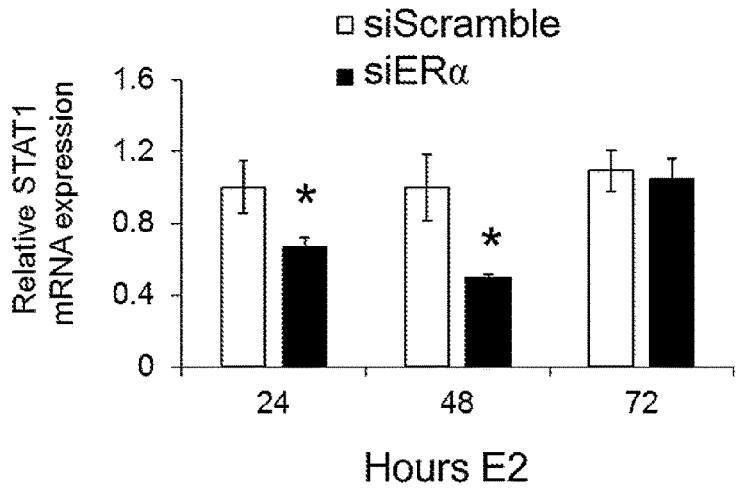

To confirm that estrogen-stimulated STAT1 expression occurs via ERα, siRNA constructs were transfected into THP-1 cells to block the production of ERα (siERα). As expected, relative to non-sense control siRNA treatment (siScramble), siERα significantly suppressed ERα transcript expression in a transient manner over multiple time points in the presence of estrogen (FIG. 2C). The kinetics of the siRNA knockdown are correlative with mathematical modeling considering the cells and conditions used. Additionally, knockdown of ERα also transiently inhibited estrogen-mediated induction of STAT1 expression. While STAT1 mRNA transcripts were reduced 33% ($p \leq 0.02$) following 24 h estrogen stimulation and 51% at 48 h ($p \leq 0.002$), no observable difference was detected at 72 h (FIG. 2D).

(4) STAT1 is Overexpressed in SLE and Activated with Estrogen Stimulation

Figure 3A:
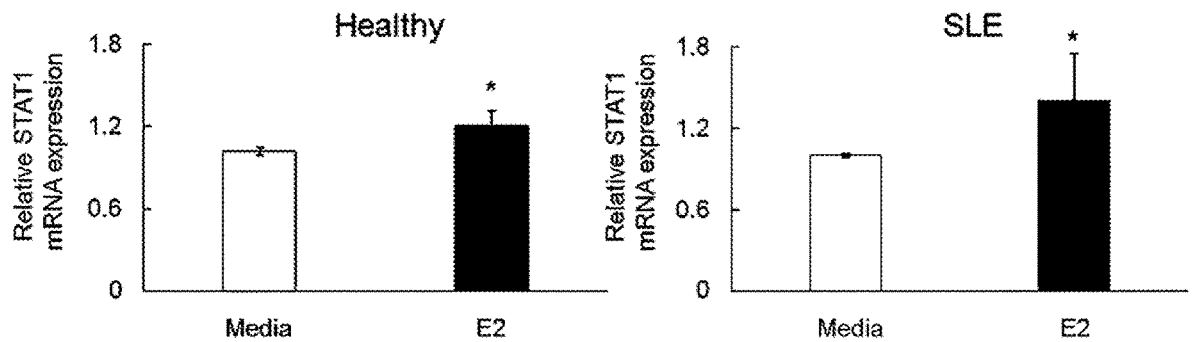
Figure 3B:
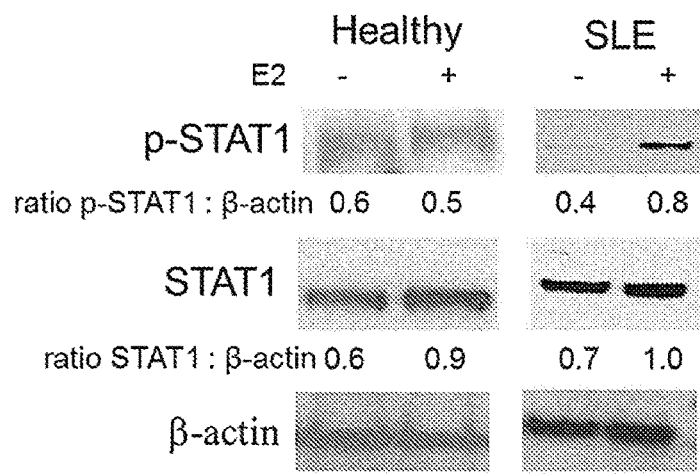

To investigate estrogen regulation of STAT1 expression in primary cells, freshly isolated PBMCs from healthy volunteers or SLE patients were treated with estrogen. While estrogen induced STAT1 mRNA transcript expression 1.2-fold (p b 0.003) in healthy subjects, this response was upregulated 1.4-fold (p b 0.01) in SLE PBMCs (FIG. 3A). Western blotting of whole cell lysates taken from these cells not only confirmed STAT1 upregulation with estrogen treatment at the protein level 1.46-fold in healthy controls and 1.35-fold in SLE, but also demonstrated enhanced phosphorylation to its activated form (p-STAT1; FIG. 3B). Interestingly, the quantitation of p-STAT1 levels showed no activation in healthy controls, but a 2-fold enhancement in PBMCs derived from SLE patients (FIG. 3B).

Figure 3C:
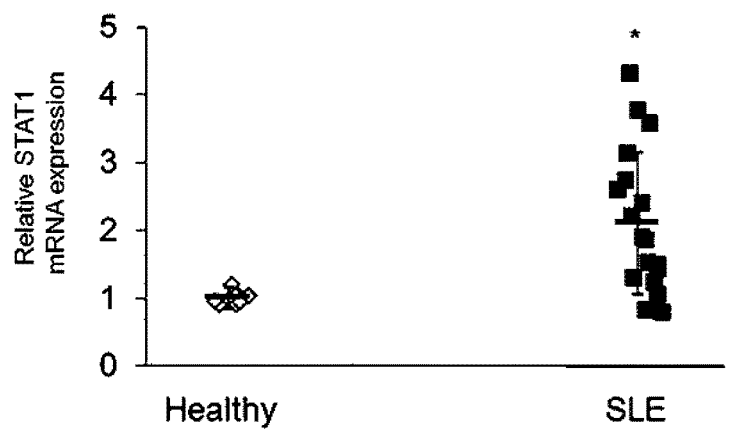

To evaluate the relationship between STAT1 expression and disease, publicly available gene chip data sets from GEO accession: GSE11909, including 156 SLE patients and 19 healthy controls were compared using Ingenuity software. Results from gene array analysis show that STAT1 expression is elevated 1.75-fold ($p \leq 0.002$) in SLE patients relative to healthy controls. In concordance, RNA isolated from whole blood of SLE patients also displayed significant enhancement of STAT1 transcript expression (2.14-fold; $p \leq 0.02$) relative to age and sex-matched healthy controls (FIG. 3C).

(5) Estrogen Induces STAT1 Transcriptional Activity Proximal to TLR8

Figure 4A:
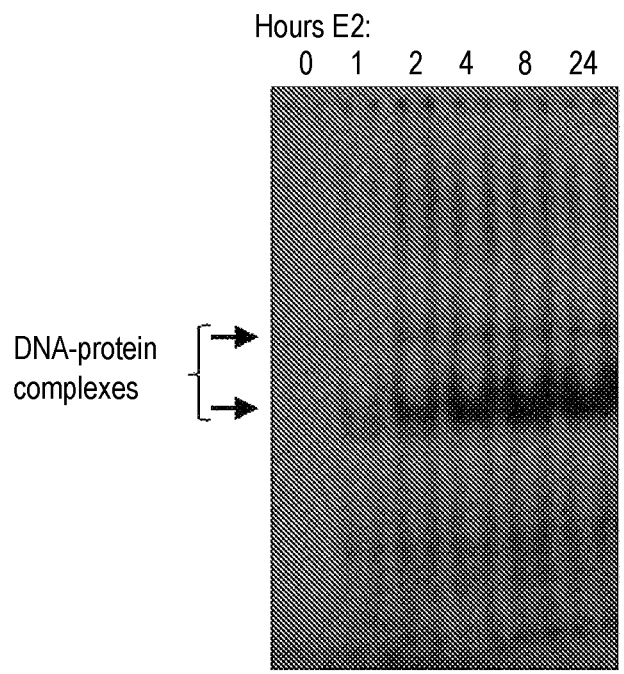
Figure 4B:
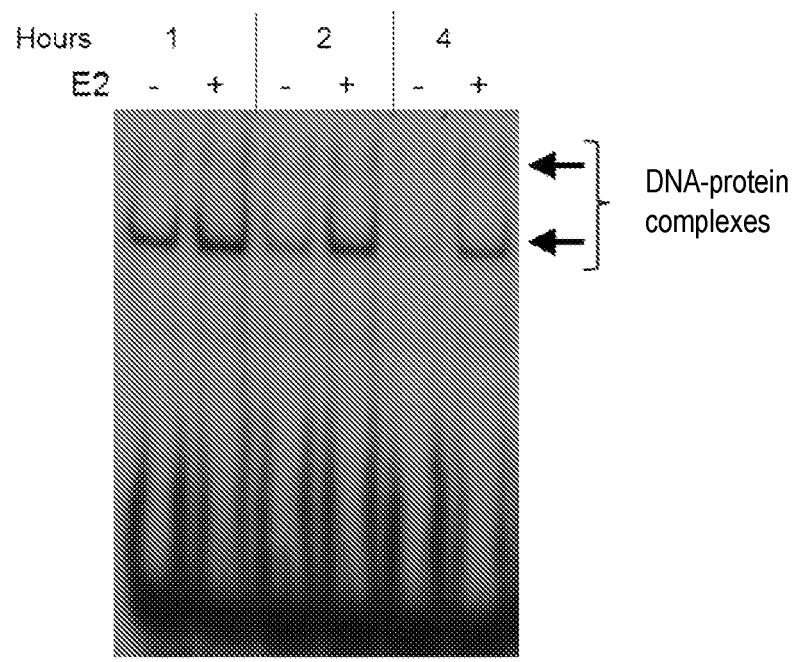

Since estrogen stimulation has been shown to enhance DNA binding of STAT1 in mouse splenocytes, the possibility of estrogen-mediated induction of STAT1 transcriptional activity was examined in human cells. The promotion of TLR8 expression via STAT1 transcriptional activation was specifically examined in this regard because i) the observation showing enhanced TLR8 expression with estrogen treatment and ii) recent studies identifying a bona fide STAT1 binding region located 24 kb from the 3' end of the TLR8 gene following treatment with a synthetic agonist (R-848). Using radio-labeled probes containing the sequences of this previously established STAT1 transcriptional binding site, THP-1 cells were stimulated with estrogen and EMSA was performed on nuclear extracts at various time points. While no DNA-protein complexes were observed at time zero, enhancement of complex formation was observed over time (FIG. 4A). Furthermore, when compared directly to untreated cells at the time points of 1 h, 2 h, and 4 h, E2 treatment also enhanced DNA-protein complexes in THP-1 cells (FIG. 4B).

Figure 4C:
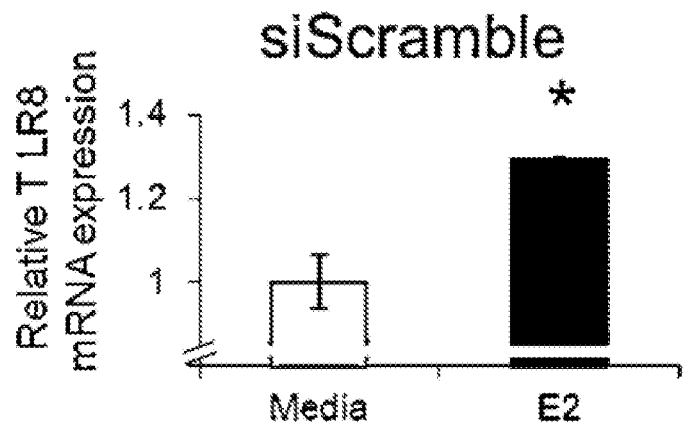
Figure 4D:
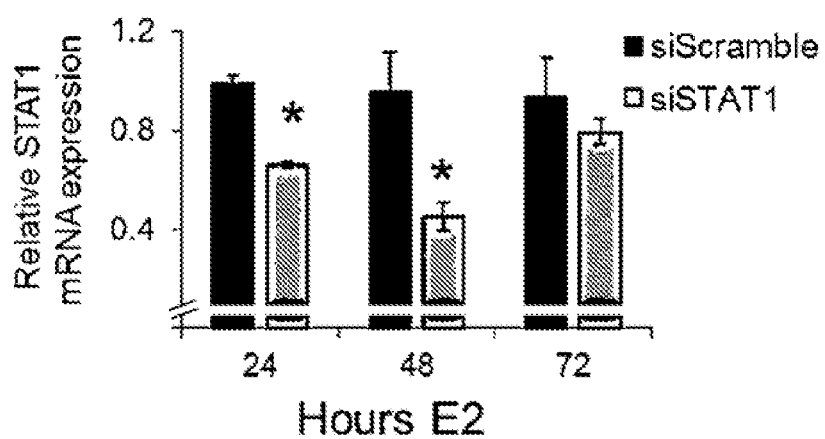

(6) Both ERα and STAT1 are Required for Estrogen-Mediated Upregulation of TLR8 Expression To demonstrate that both ERα and STAT1 are necessary for estrogen-induced TLR8 expression, siRNAs targeting STAT1 and ERα were transfected into THP-1 cells that were treated with estrogen. As a negative control, non-sense siRNA (siScramble) was used, which did not inhibit the estrogen-induced expression of TLR8 in THP-1 cells; here, estrogen still up-regulated TLR8 transcripts by 1.35-fold (p b 0.05; FIG. 4C). To confirm that siRNA blocking STAT1 (siSTAT1) significantly inhibited its expression in THP-1 cells, STAT1 expression was measured over time. Relative to siScramble-transfected cells, siSTAT1 transiently suppressed STAT1 expression with estrogen treatment according to the predicted kinetics under these conditions (FIG. 4D).

Figure 4E:
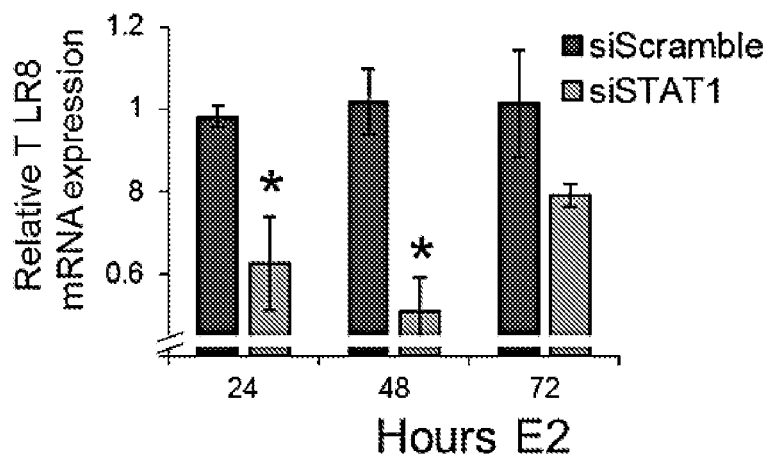
Figure 4F:
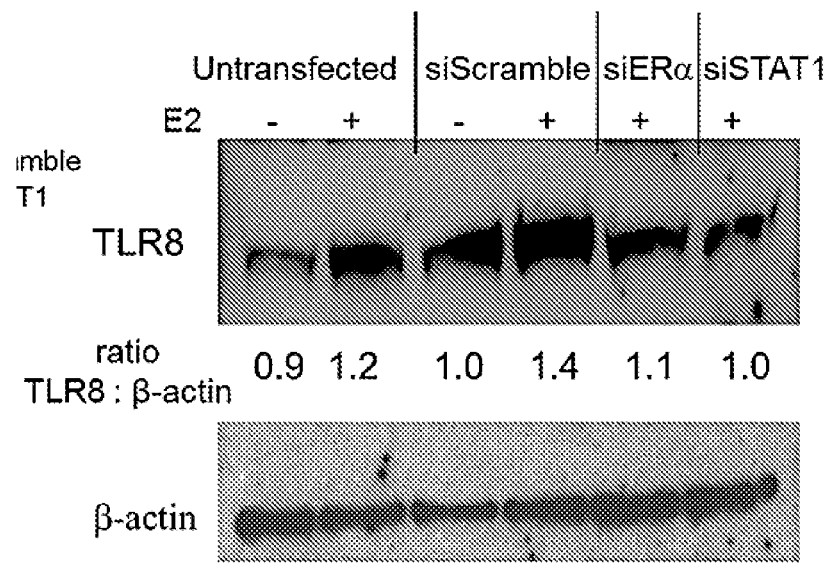

With STAT1 expression suppressed in THP-1 cells, estrogen-mediated TLR8 expression was also significantly inhibited. Relative to siScramble controls, detection of TLR8 transcripts showed a reduction of 38% at 24 h ($p \leq 0.05$), 49% at 48 h ($p \leq 0.02$), and 21% at 72 h following estrogen stimulation (FIG. 4E). To demonstrate this effect at the protein level, whole cell lysates were collected from estrogen-treated THP-1 cells. Both un-transfected and negative controls (siScramble) displayed enhanced TLR8 expression with estrogen stimulation by 1.38 and 1.33-fold, respectively (FIG. 4F). However, siRNA targeting either STAT1 or ERα suppressed this response back to untreated control levels (FIG. 4F).

(7) miR-21 Stimulates TLR8 Activation

Figure 5A:
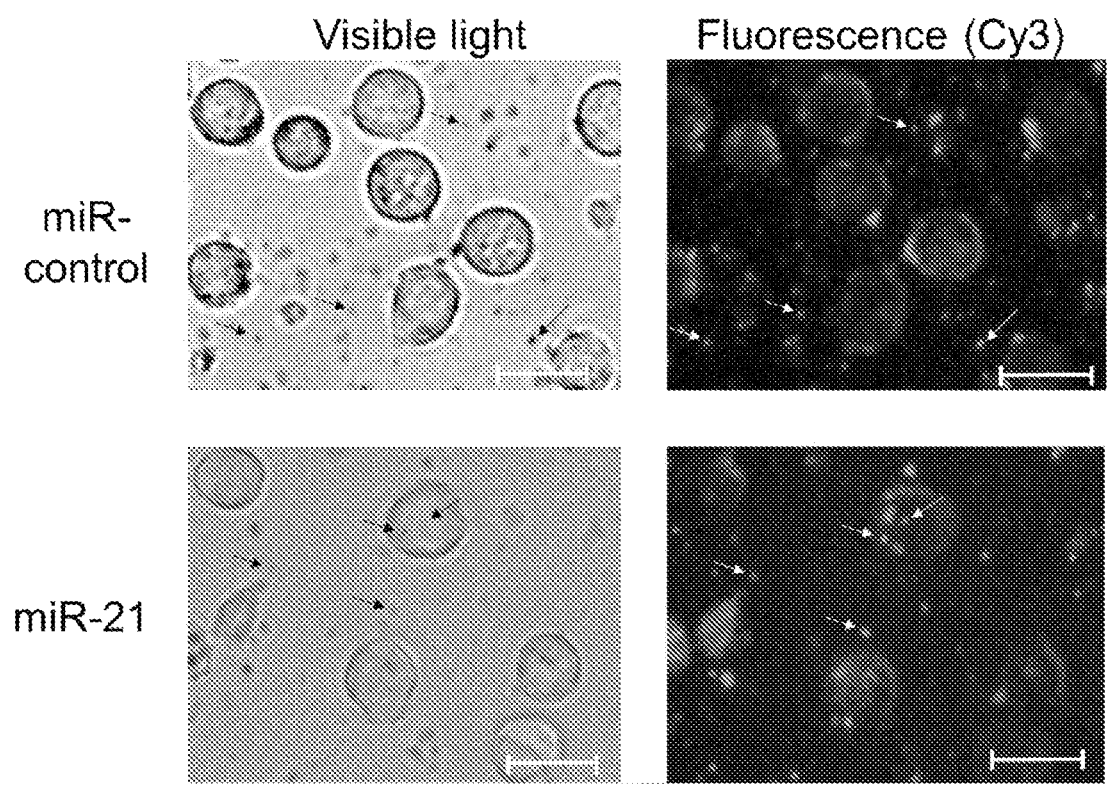
Figure 5B:
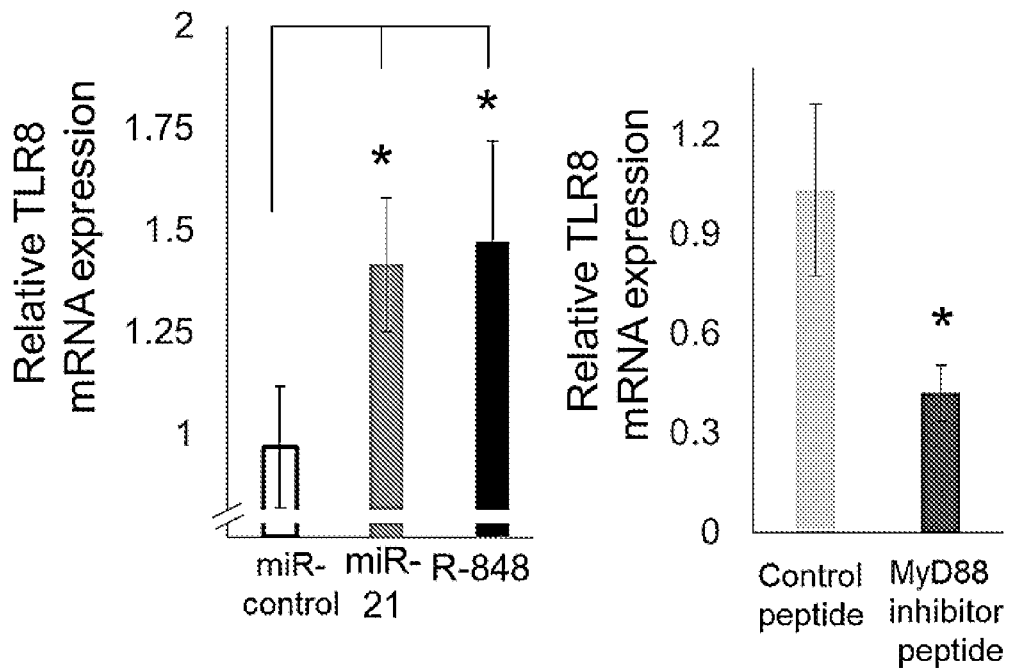

In the absence of TLR8 activation, estrogen-mediated upregulation would be inconsequential and without downstream signal transduction. In lieu of ssRNA of viral origin, recent studies have shown that miR-21 can function as an endogenous agonist for TLR8 to promote carcinogenesis by being packaged and secreted in EVs. Since this signaling pathway utilizes miRs that are packaged in EVs, synthetically produced vesicles (pseudoexosomes) were designed by encapsulating ssRNA conjugated to cyanine (Cy)3 in liposomes. Following 6 h incubation with THP-1 cells, these small vesicles containing miR-21 or nonsense control (miR-control) can be visualized using fluorescence microscopy in the medium and in close proximity to cells (FIG. 5A). Subsequently, TLR8 expression and cytokine activation were examined to characterize the downstream effects of vesicle-encapsulated miR-21 signaling in macrophages. Expression of TLR8 was measured specifically because treatment of hematopoetic cell lines and primary PBMCs with synthetic agonist (R-848) results in significantly enhanced expression. After 24 h, stimulation of THP-1 cells with miR-21 pseudoexosomes or R-848 significantly induced transcript expression of TLR8 by 1.4-fold ($p \leq 0.05$) and 1.5-fold ($p \leq 0.05$) relative to treatment with miR control pseudoexosomes, respectively (FIG. 5B). To demonstrate a direct association with TLR8 signaling in this response, THP-1 cells were stimulated with liposome encapsulated miR-21 and treated with a protein inhibitor for myeloid differentiation primary response gene (MyD)88, which is an adaptor molecule that interacts with TLR8 immediately downstream. Compared to treatment with control peptide, TLR8 mRNA expression levels were reduced by 58% ($p \leq 0.001$) with MyD88 inhibition (FIG. 5B).

Figure 5C:
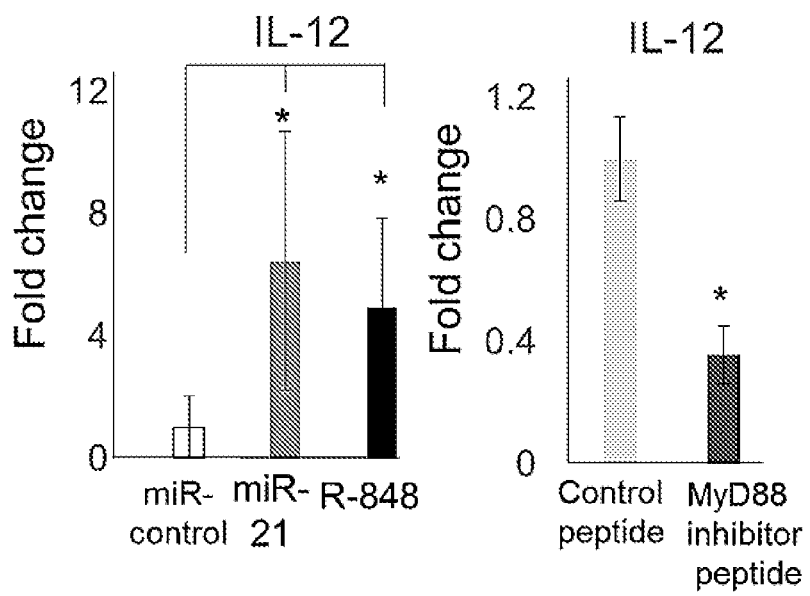
Figure 5D:
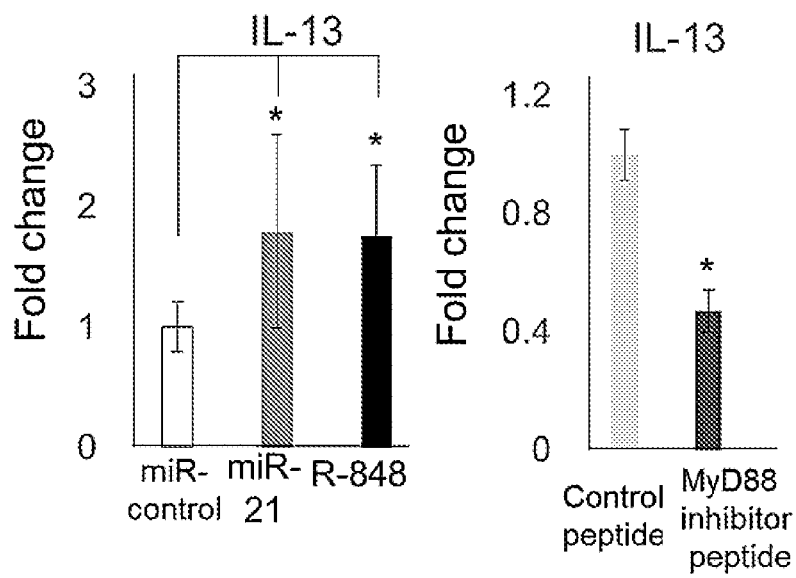

According to previous studies, agonist-mediated TLR8 signaling leads to the production of IL-12 and IL-13. Therefore, the secretion of these cytokines was analyzed in THP-1 cells by ELISA following stimulation with either miR-21 pseudoexosomes or R-848. IL-12 expression was induced 6.4-fold (p b 0.02) by miR-21 and 5-fold (p b 0.05) by R-848 compared to control treatment (FIG. 5C). Furthermore, inhibition of MyD88 led to a 64% (p b 0.02) reduction in miR-21-induced IL-12 expression (FIG. 5C). Additionally, miR-21 and R-848 treatment upregulated IL-13 expression 1.8-fold (p b 0.05) and 1.75-fold (p b 0.05) relative to cells treated with miR-control pseudoexosomes, respectively (FIG. 5D). However, when THP-1 cells were stimulated with miR-21-containing vesicles and treated with MyD88 inhibitor, IL-13 secretion was reduced by 29%0 (p b 0.001; FIG. 5D).

Figure 5E:
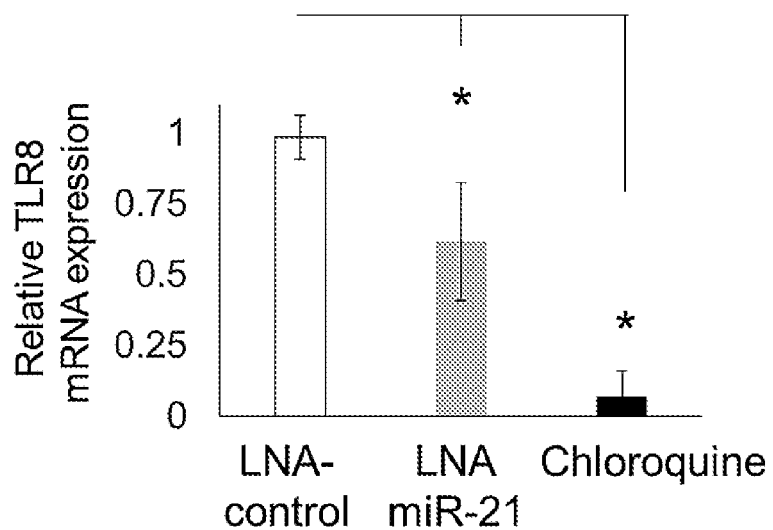

To examine the effects of EV-derived miR-21 in primary cells, EVs were isolated from pre-menopausal SLE patients and age/sex matched healthy female controls. In addition, miR-21 expression levels were also measured from whole blood samples. miR-21 was detected in both analyses and the expression did not change significantly in SLE patients relative to healthy controls after normalization to total RNA. To determine the effect of antagonizing miR-21, primary human macrophages derived from healthy donors were treated with liposomal complexes containing locked nucleic acid (LNA) sequences designed to block miR-21 (LNA antagomiR-21). LNAs are RNA nucleotides containing a modified ribose moiety and were used to antagonize miR functionality here because they are significantly more resistant to enzymatic degradation than RNA. Cells were incubated with autologous serum as an endogenous source of EV-derived miR-21 for 24 h. Relative to nonsense control treatment (LNA-control), inhibition of miR-21 with LNA antagomiR-21 reduced the expression of TLR8 mRNA by 46% ($p \leq 0.05$; FIG. 5E).

While antimalarial drugs, including chloroquine, have been used to treat patients with SLE for over 70 years, the mechanism of action has never been fully understood. Recent evidence indicates that chloroquine is not functioning by altering endosomal pH to prevent intracellular TLR activation, but rather is binding to nucleic acids directly to mask antigenic epitopes. To assess the effectiveness of chloroquine in suppressing TLR8 expression induced by EV-derived miRs in autologous serum, transcript levels were measured in primary human macrophages following 24 h incubation. Chloroquine treatment resulted in a reduction of TLR8 expression by over 95% ($p \leq 0.005$) compared to the LNA-control condition (FIG. 5E).

(8) miR-21 Stimulates Extracellular Vesicle Secretion

Figure 6A:
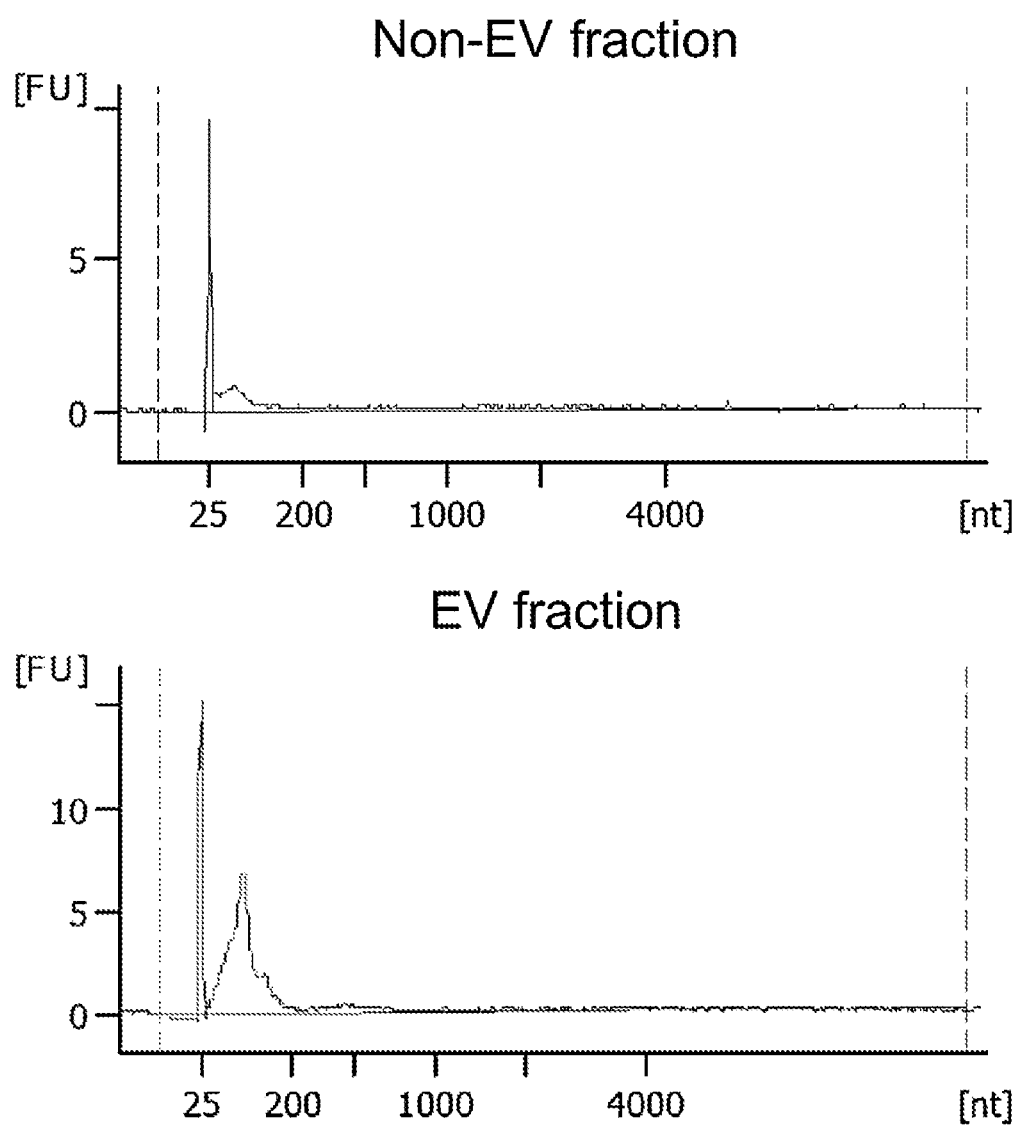
Figure 6B:
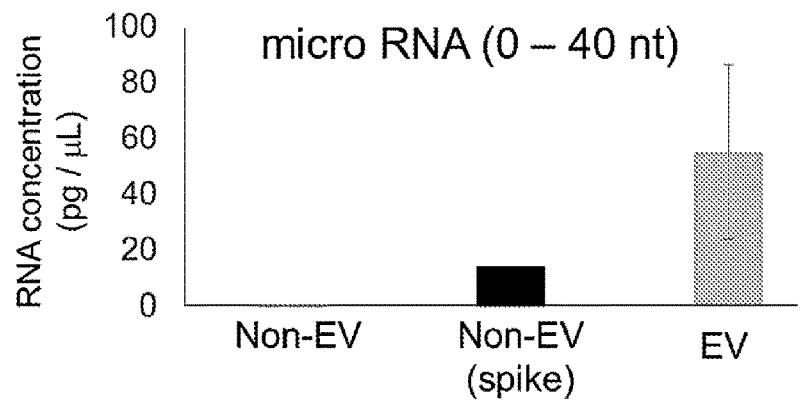
Figure 6B:
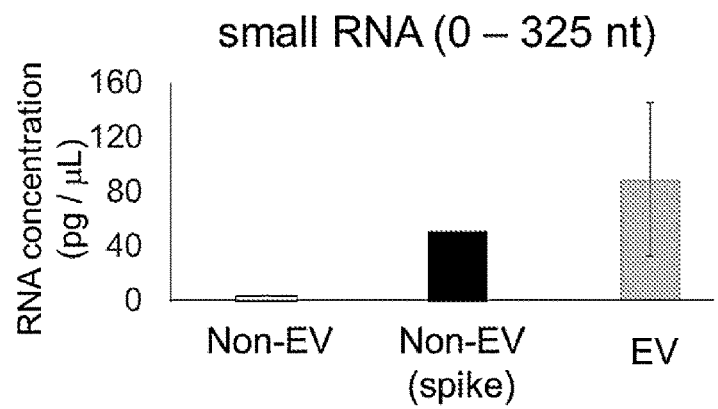
Figure 6C:
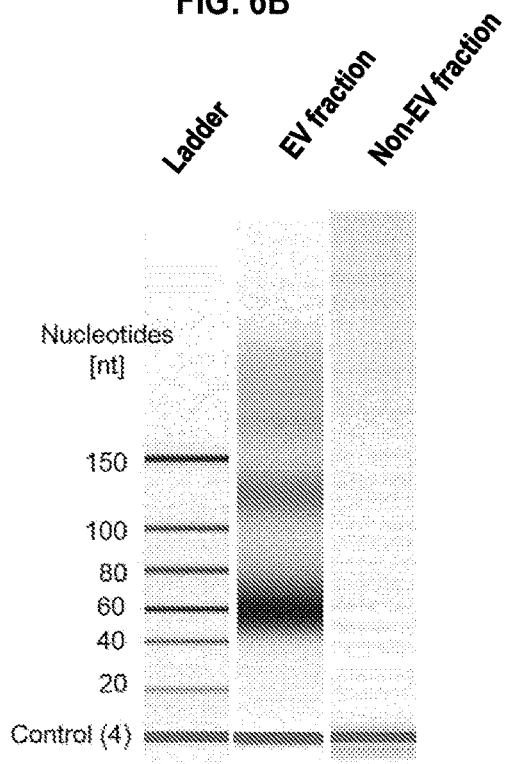

Given the newfound cell-to-cell communication and signaling functionality of EVs by delivering RNA to recipient cells, the extracellular fractions isolated from blood of SLE patients was examined to determine the precise localization of small RNA sequences. Following EV isolation and total RNA purification procedures allowing for efficient recovery of small RNA (<200 nt) species, samples were analyzed by nanofluidics to measure RNA quantity, size, and integrity. While the micro (0-40 nt) and small (0-325 nt) RNA recovered from non-EV extracellular fractions were almost undetectable (maximum of 4.8 pg/μL), that which was found in the EV fraction was approximately 20 times greater (90 pg/μL) (FIG. 6A). To ensure that the non-EV RNA fractions were not degraded or lost during experimental processing, samples were supplemented (spike) with cellular RNA isolated with the same protocol and recovery was confirmed (FIG. 6B). Furthermore, the RNA recovered from the EV fraction was not degraded, as demonstrated by distinct bands on the electrophoretic gel image (FIG. 6C).

Figure 6D:
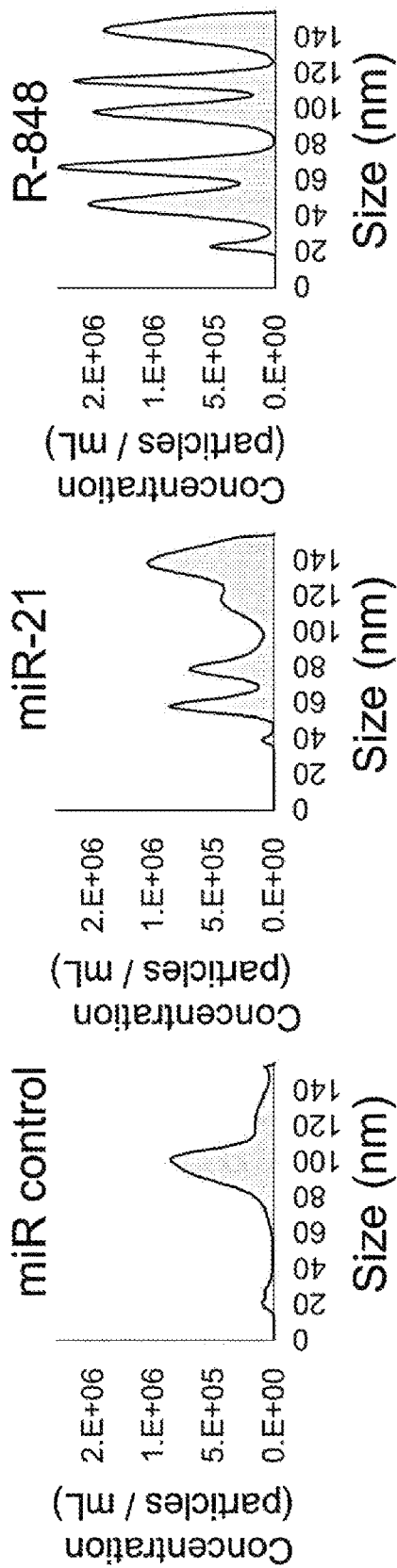
Figure 6D:
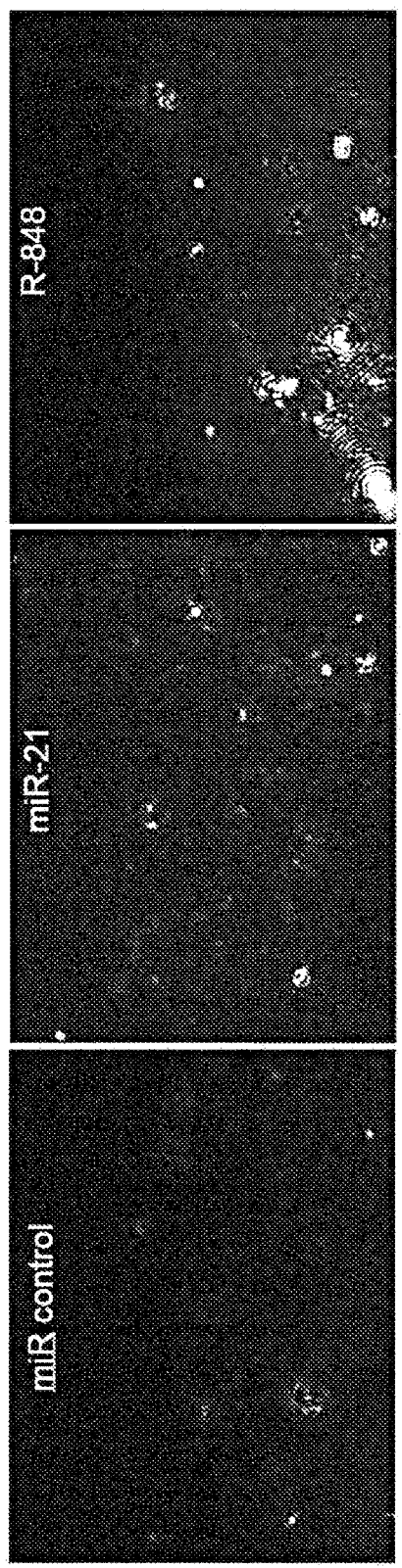
Figures 6D, 6E:
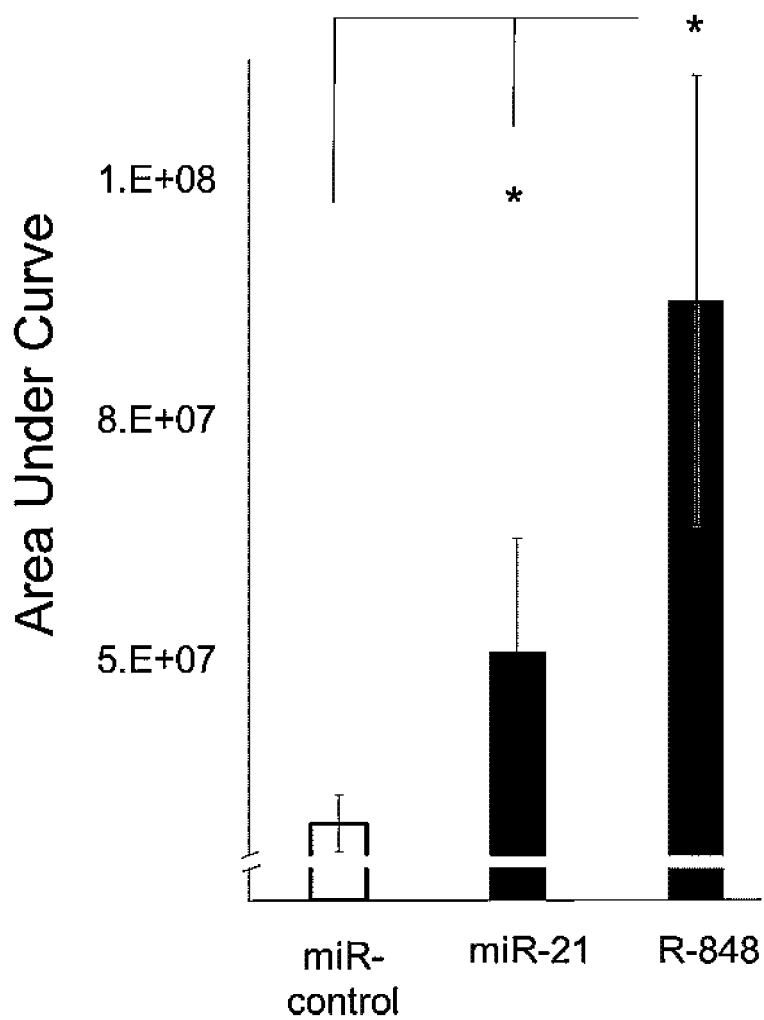

The key role that EVs can play in regulating inflammation through the delivery of bioactive molecular cargo has only recently been proposed in the past decade. Furthermore, although exosome biogenesis originates from intracellular endosomes, which is the precise cellular localization of all nucleic acid-binding TLRs (TLR3, TLR7, TLR8, and TLR9), the effect of TLR activation on EV production has yet to be investigated. THP-1 cells were treated with miR-21 pseudoexosomes or R-848 and extracellular particle profiles (EPPs) were measured using NTA to quantitate EV production. Relative to treatment with miR-control, stimulation by miR-21 and R-848 significantly induced particles ranging from 0 to 160 nm in diameter (FIG. 6D). Specifically, the cumulative EPPs resulting from miR-21 and R-848 induction were increased by 2.0-fold ($p \leq 0.05$) and 3.7-fold ($p \leq 0.01$), respectively (FIG. 6E).

c) Discussion

Epidemiological data shows that the incidence of SLE peaks in females when levels of estrogen are highest. Specifically, disease predilection for women is nine times higher in pre-menopausal females when compared to age-matched males, but drops significantly during pre-adolescence or post-menopause. Consequently, it has been suggested that hormones, particularly estrogen, can be one of the contributing factors leading to disease pathogenesis.

While estrogen can induce TLR8 upregulation through ERα binding to an ERE proximal to the TLR8 genetic locus, these data outline a more comprehensive mechanistic understanding through an association with STAT1 expression and transcriptional activity. In the model of TLR8 activation and signaling in SLE, estrogen (E2) enters the cell and binds to estrogen receptor ERα. The resulting dimers translocate to the nucleus and promote either STAT1 or TLR8 expression by transcriptional activation through ERE binding. STAT1 expression and activation by estrogen leads to transcriptional activation of TLR8 expression, which can be triggered by an endogenously-derived and EV-encapsulated miR-21 ligand. While the conventional role of miRs is to function as a complimentary sequence targeting specific cytoplasmic mRNAs to neutralize expression, the signaling pathway through TLR8 activation represents a non-conventional role for miRs to function within cells.

Figure 7:
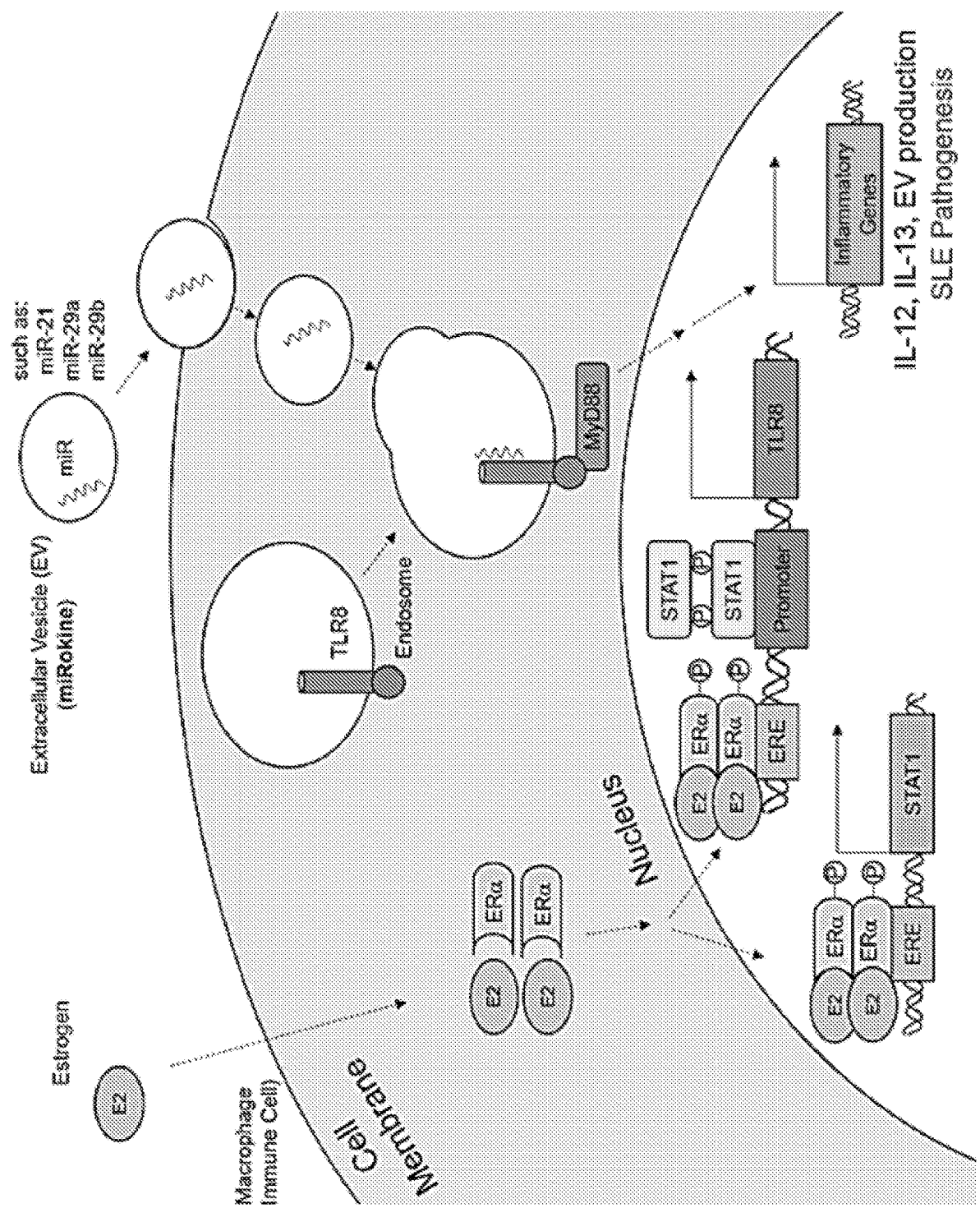
FIG. 7 shows TLR8-mediated signal transduction through the MyD88 pathway can ultimately result in production of EVs.

TLR8-mediated signal transduction through the MyD88 pathway can ultimately result in production of EVs and enhanced expression of IL-12, IL-13, and other inflammatory genes that can function to promote SLE pathogenesis (FIG. 7). Thus, intracellular miRs are packaged and secreted in EVs to facilitate autocrine or paracrine immunomodulatory responses through communication as extracellular mediators. Considering the evolution of nomenclature following the discovery and characterization of cytokines, which resulted in the establishment of terminology including chemokines, myokines, and adipokines, the term miRokine refers herein to this signaling process. In this manner, EV-derived miRs can function as secreted inflammatory mediators, or miRokines, to signal between cells.

While the biogenesis and secretion of EVs were characterized nearly 30 years ago, packaging and secretion of miRs in EVs to induce changes in recipient cells have only been described in the last decade. Aside from being contained within EVs, extracellular RNA can presumably exist freely or can be bound into ribonucleoprotein complexes.

EVs and chaperone proteins offer protection against enzymatic degradation, which is critical to extracellular stability considering that free RNA is completely degraded within minutes due to the high level of ribonuclease activity physiologically. Results from primary human samples have been contradictory in demonstrating whether extracellular miRs are found in greatest abundance in EVs or associated with proteins outside of EVs, but this can be attributable to the methodology of EV isolation, disease state, and the limitations associated with analyzing only specific RNA sequences in these studies. Here, EVs were isolated from human SLE samples and investigated the total recovery of all small RNA sequences (0-325 nt). While RNA was also detected in the non-EV fraction, the greatest recovery was observed to be EV associated.

In concordance with the results, treatment with lipid destabilizing detergents show a significantly reduced detection of miRs from conditioned media of THP-1 cells and RNA from human plasma samples.

In addition to regulating the expression of many genes, estrogen also has the potential to transcriptionally modulate miR production. Interestingly, of the many miRs observed to be induced by estrogen, miR-21 is up-regulated 2-fold.

These data demonstrate that treatment with liposomal encapsulated miR-21 significantly stimulated IL-12, IL-13, and TLR8 expression and that this was suppressed with MyD88 inhibition, which suggests a direction association with the TLR8-mediated signaling pathway. Considering that levels of IL-12 and IL-13 are elevated in SLE patient serum and have been associated with disease activity, these results indicate that this can be a consequence of EV-encapsulated miR-21 activation of TLR8 signaling. Therefore, the pleotropic effects of estrogen can promote immune activation both by upregulating TLR8 as well as the in vivo-generated ligand. Considering the strong association of dysregulated miR expression in SLE and that miR-21 deficiency has been shown to protect from lupus-like autoimmunity in a mouse model, targeting miR-21 and any additional miRs potentially functioning as TLR ligands represents a novel therapeutic strategy to suppress inflammation in SLE.

Antimalarial drugs have been shown to reduce disease activity and have been used routinely to treat SLE for over half a century, but the mechanism of action has yet to be conclusively elucidated. Suppression of TLR activation by chloroquine was initially attributed to the inhibition of endosome acidification, but recent data demonstrates that endosomal TLR activation was inhibited by chloroquine through the direct binding of nucleic acids within endosomal compartments. The data shows that while suppression of TLR8 expression was observed with chloroquine or anti-miR-21, chloroquine significantly reduced TLR8 expression to a much greater extent than by blocking miR-21 alone. Collectively, these data suggest that chloroquine can be binding to miRs to prevent TLR8 induction within endosomal compartments and that multiple miRs are most likely capable of TLR8 activation in this system. To suppress the effect of miR-21, a miR antagonist was designed with a modified LNA backbone, which enhances resistance to degradation when compared to RNA and has been shown to persist in vivo for over a week.

Figure 8:
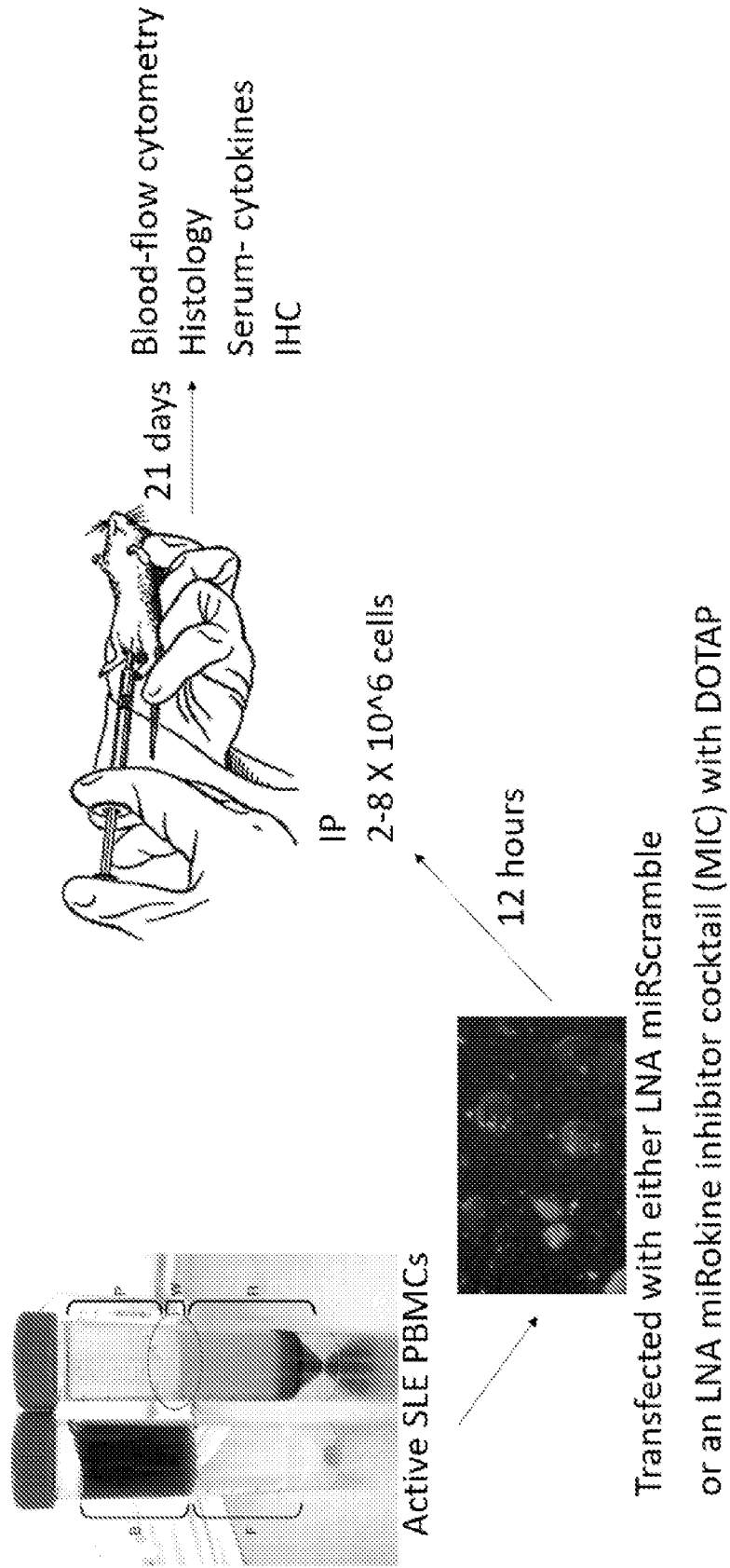
FIG. 8 shows a schematic representation of the creation of a murine SLE model.

2. Example 2: Novel Therapeutic Inhibitor Cocktail Suppresses Extracellular Vesicle-Mediated Inflammation Induced by Micro-RNA in a Humanized Mouse Model of Lupus a) Results To explore the therapeutic potential of antagonizing TLR7 and TLR8 inflammatory pathways induced by extracellular vesicle (EV)-derived miRNAs, 2-8×10$^6$ PBMCs from active SLE patients were injected into immunodeficient NOD-scid IL-2rγ (null) mouse recipients to produce chimeras containing PBMCs from SLE patients (FIG. 8). Prior to injection, PBMCs were incubated with synthetically produced, liposomal EVs containing either a cocktail of locked nucleic acid miRNA antagonists (i.e., anti-miR-21 (SEQ ID NO: 1), anti-miR-29a (SEQ ID NO; 2), and anti-miR-29b (SEQ ID NO; 3)) or a nonsense control. After 21 days, blood was collected for both flow cytometry and cytokine analysis and tissues were processed for histopathological examination by H&E and immunohistochemistry.

Figure 9A:
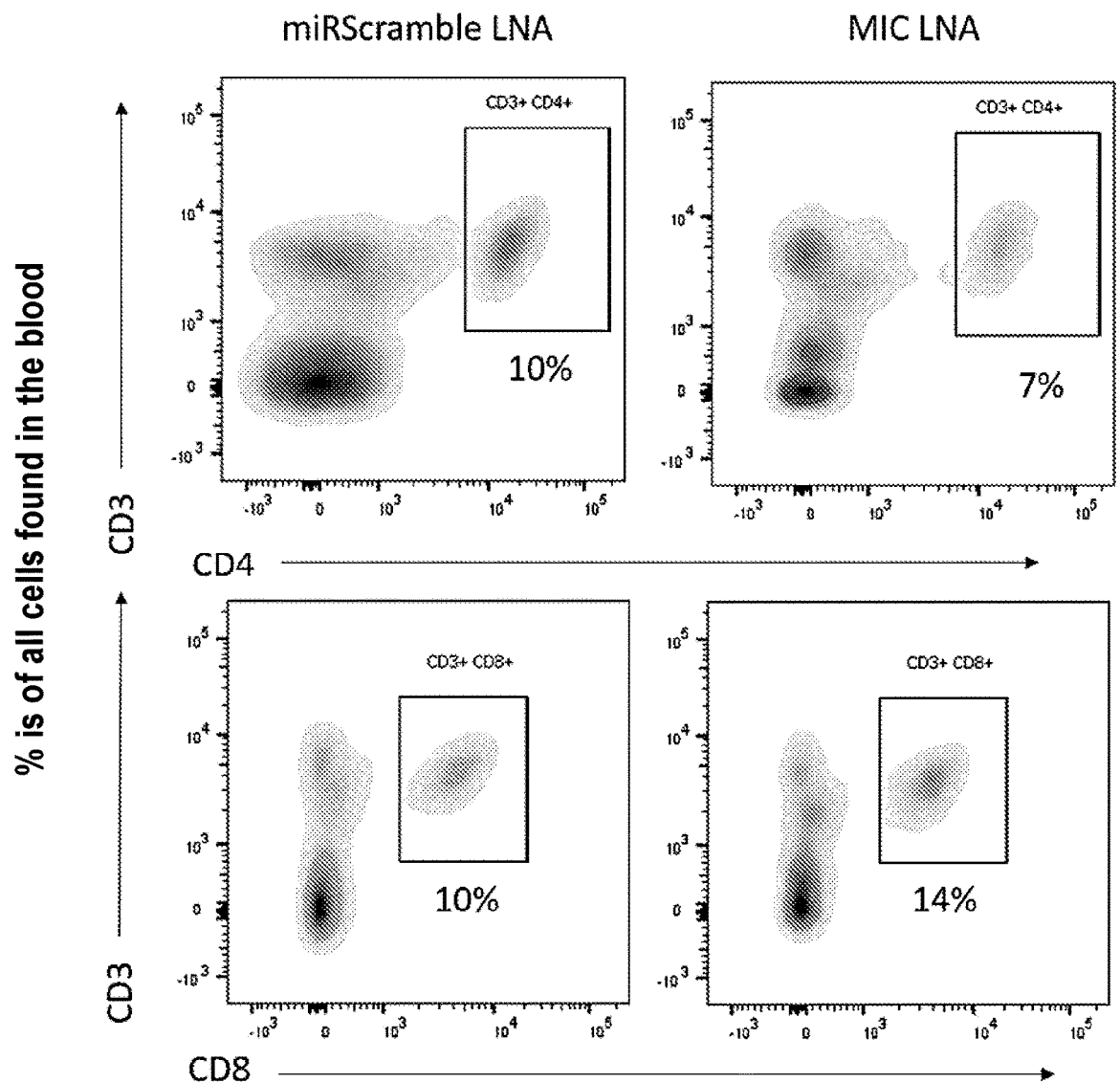
FIG. 9A shows the percentage of CD4 and CD8 T cells in immunodeficient NOD.Cg-Prkdcscid Il2rgtmlWj1/SzJ (NSG) mice receiving human SLE cells in combination with either with locked nucleic acid miR antagonists or a nonsense control 21 days after transfer of cells.
Figure 9B:
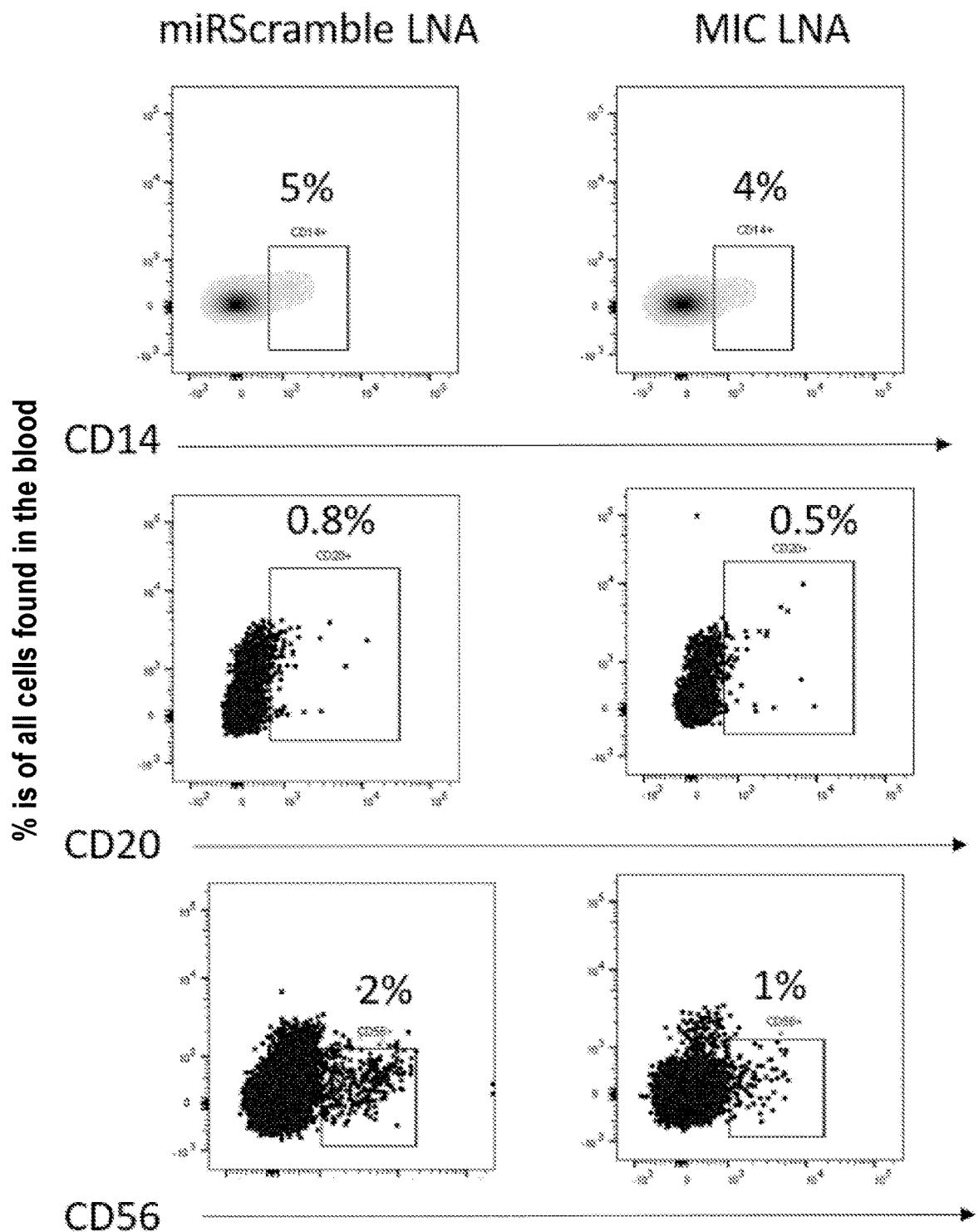
FIG. 9B shows that expression of CD14, CD20, and CD56 does not vary between NOD-scid IL-2rγ mice receiving human SLE cells in combination with either with locked nucleic acid miR antagonists or a nonsense control 21 days after transfer of cells.

The microRNA inhibitor cocktail (MIC) LNA treatment and miRScramble LNA both permitted successful engraftment of human cells. 21 days following transfer of human SLE cells, Human T-cells (CD4+ and CD8+), B-cells (CD20), monocytes (CD14), and NK cells (CD56) were all successfully recovered from whole blood of chimeric mice at similar levels in both treatment groups (FIGS. 9A and 9B).

Figure 10:
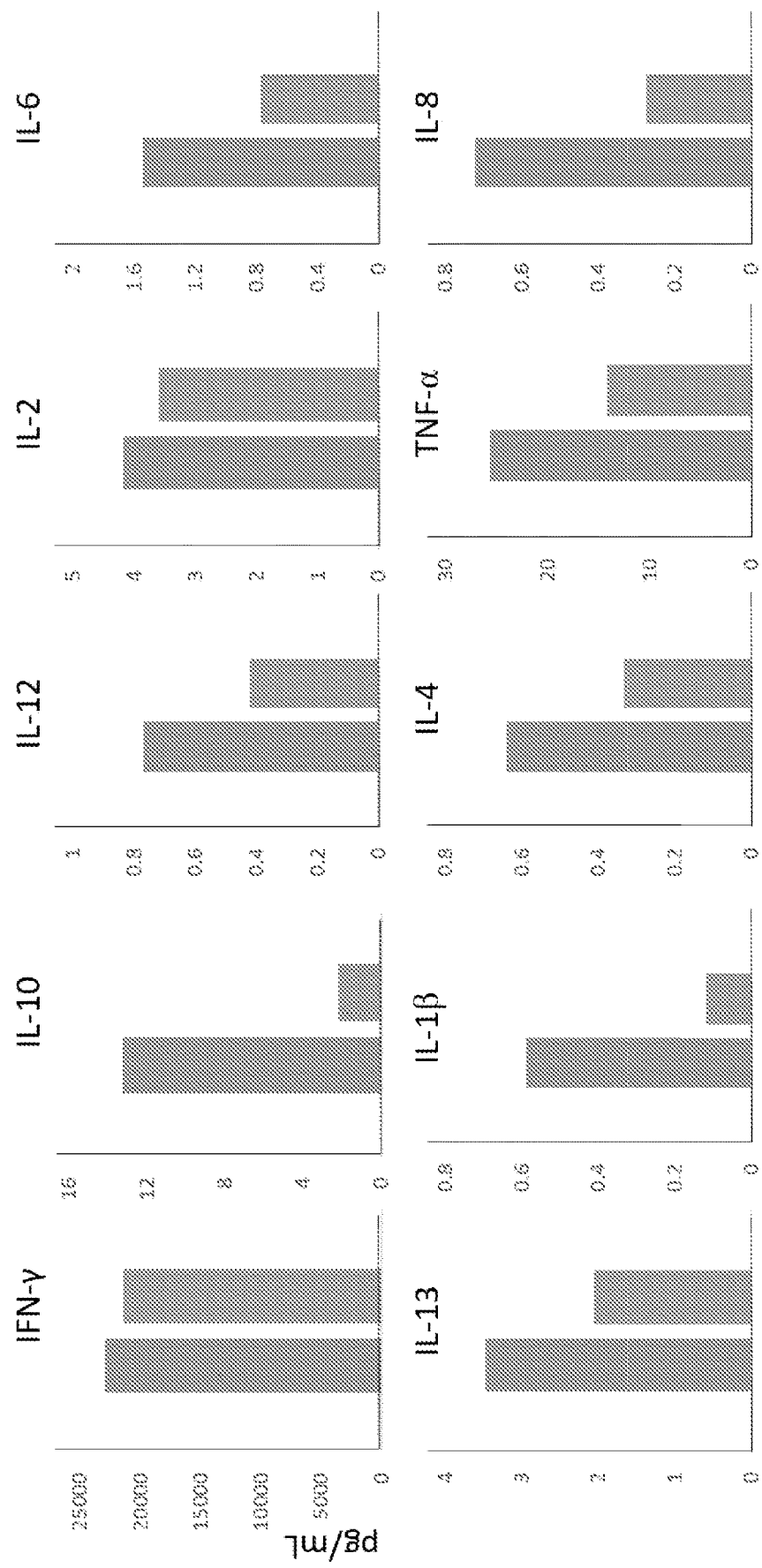
FIG. 10 shows the cytokine expression 21 days after transfer of SLE cells in combination with either with locked nucleic acid miR antagonists or a nonsense control into NOD-scid IL-2rγ mice.
Figure 11A:
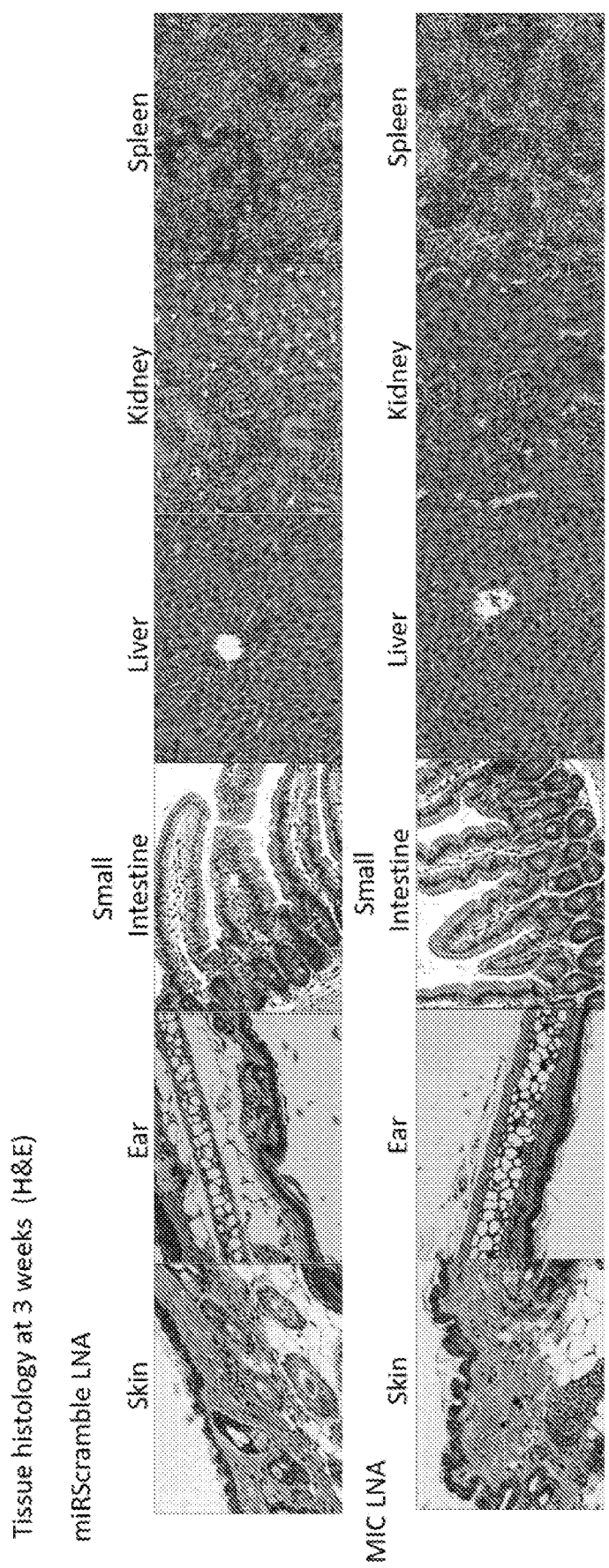
FIGS. 11A and 11B show histopathological examination of small intestine, lung, and kidney.
Figure 11B:
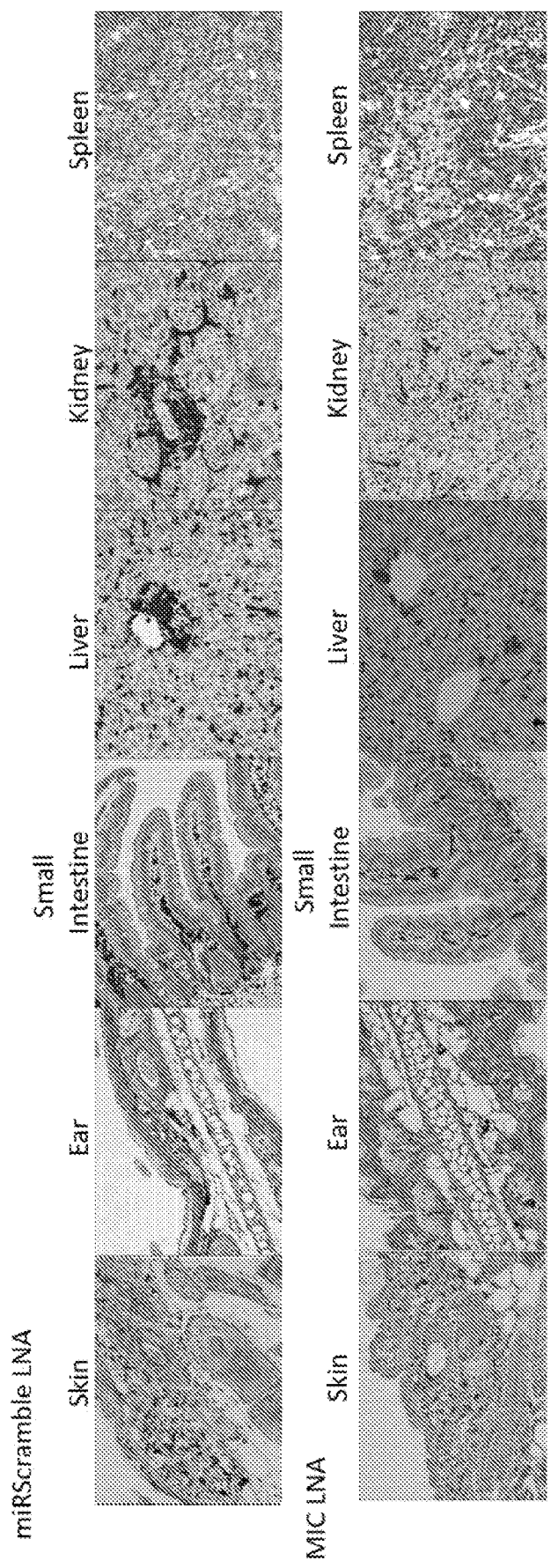

However, while T cells, B cells, and NK cells were recovered at similar levels in both groups of mice, cytokine expression was reduced with MIC LNA treatment relative to miRScramble LNA in the serum. Specifically, while IFN-γ suppression was minimal, the level of human IL-2, IL-6, IL-10, and TNF-α were reduced with miRNA inhibition when compared to control treatment (FIG. 10). Although histopathological analysis revealed little to no inflammation in the skin and ear, a robust response was detected in the small intestine, liver, and kidney, which was markedly reduced with miRNA inhibition using the MIC (FIGS. 10A (H&E) and 11B (Immunohistochemistry). Additionally, staining for human CD3 confirmed T-cell presence in these infiltrates (FIG. 11B).

These results establish also establish a chimeric model to study the inhibition of EV-encapsulated miRNAs that bind to TLR7 and TLR8 and to explore their therapeutic efficacy in suppressing innate immunity in SLE.

b) Materials and Methods (1) Human Samples and PBMC Isolation

Patients meeting the revised American-European consensus criteria for SLE as well as age and sex-matched healthy volunteers (n=4) were recruited for the study from The Ohio State University Wexner Medical Center (OSUWMC) clinics, the Research Match program at OSUWMC, and the American Red Cross. Participation was through an approved Institutional Review Board protocol. PBMCs were isolated under Ficoll gradient centrifugation.

(2) Mice 4-week old NOD.Cg-Prkdcscid Il2rgtm1Wj1/SzJ (NSG) mice were obtained from The Jackson Laboratories. All animal maintenance and protocols are approved by the Institutional Animal Care and Use Committee at OSUWMC. Animal facility was maintained at 22-23° C. and between 30 and 50% relative humidity with a 12-hour light/dark cycle. Chow and water were available ad libitum.

(3) Adoptive Transfers

Freshly isolated human PBMCs were injected intraperitoneally into 8-week old NSG mice ($2-8 \times 10^6$ cells/mouse). Human PBMC preparations were washed in PBS and counted using a hemocytometer with trypan blue to ensure cell viability. All samples were kept separate and not pooled before injections. Mice were monitored every other day, including weights and physical signs of disease progression, and sacrificed 4 weeks after adoptive transfer for blood and tissue collection as described below.

(4) Tissue Collection and Staining

Mouse tissues were dissected, submerged in neutral buffered 10% formalin, and transferred to 70% ethanol for paraffin processing. Paraffin blocks were cut at 4 microns, placed on positively charged slides, and fixed in cold acetone. Serial paraffin sections were used for immunohistochemistry and hematoxylin and eosin (H&E) staining. Briefly, all slides were stained in Richard Allan Scientific Hematoxylin (Thermo Scientific, Waltham, MA) and Eosin-Y (Thermo Scientific) with the Leica Autostainer (Leica Biosystems, Buffalo Grove, IL). Immunohistochemistry was performed with antibodies for CD4 (Leica Biosystems), CD8 (Dako, Carpinteria, CA) CD20 (Dako), and CD68 (Dako) using the Dako Autostainer system according to manufacturer's protocol.

(5) Image Analysis and Histopathology Scoring

Slides were scanned using the Aperio ScanScope XT eSlide capture device (Aperio, Vista, CA). H&E-stained paraffin sections were subjected to blinded histopathological analysis by a board-certified veterinary pathologist.

(6) Flow Cytometry

Blood was collected from chimeric mice by submandibular bleeding and leukocytes were purified for flow cytometry using red blood cell lysis solution (eBioscience, San Diego, CA) following the manufacturer's protocol. Cells were labeled with antibodies for anti-human CD3 (eBioscience), CD4 (Immunotech, Vaudreuil-Dorion, Canada), CD8 (Caltag Laboratories, Buckingham, United Kingdom), CD20 (eBioscience), CD14 (eBioscience), or CD56 (eBioscience) following the manufacturer's protocol. Data was collected on the BD FACS Calibur platform (BD Biosciences, San Jose, CA) using CellQuest Pro (v5.1, BD Biosciences) and exported for analysis via FlowJo (v. 7.6.5, Tree Star, Inc, Ashland, OR).

(7) Cytokine ELISA

Cytokine analysis was performed on serum collected from chimeric mice at the time of sacrifice using a cocktail of Bio-Plex Pro® single-plex magnetic beads (Bio-Rad, Hercules, CA) on the Bio-Plex 200 system according to the manufacturer's protocol. Data analysis was performed using Bio-Plex Manager® (v5.0) software and results were exported to Microsoft Excel (v2010) for further analysis.

E. Sequences

```
SEQ ID NO: 1 - anti-miR-21
CAACATCAGTCTGATAAGCT

SEQ ID NO: 2 - anti-miR-29a
AACCGATTTCAGATGGTGCT

SEQ ID NO: 3 - anti-miR-29b
ACTGATTTCAAATGGTGCT

SEQ ID NO: 4: STAT1 Forward Probe
GGGAGAATCTAGGTCAAGGTCCTTC

SEQ ID NO: 5: STAT1 Reverse Probe
GAAGGACCTTGACCTAGATTCT

SEQ ID NO: 6: TLR8 forward probe
GGGCTTTATTCTCTGAAACACCCACT

SEQ ID NO: 7: TLR8 reverse probe
AGTGGGTGTTTCAGAGAATAAAG

SEQ ID NO: 8: miR-21 mimic
UAGCUUAUCAGACUGAUGUUGA

SEQ ID NO: 9: miR-scramble
UAAGGCUAUGAAGAGAUAC
```

What is claimed is:

1. A human microRNA antagonist cocktail comprising human anti-miR-21 (SEQ ID NO: 1), human anti-miR-29a (SEQ ID NO: 2), and human anti-miR-29b (SEQ ID NO: 3).

2. The microRNA antagonist cocktail of claim 1, further comprising 1,2-Di-(9Z-octadecenoyl)-3-trimethylammonium propane methyl sulfate (DOTAP).

3. A method of treating SLE comprising administering to a subject with SLE the microRNA inhibitor cocktail of claim 1.

* * * * *